United States Patent
Yang et al.

(10) Patent No.: US 8,796,308 B2
(45) Date of Patent: Aug. 5, 2014

(54) MODULATORS OF CYSTIC FIBROSIS TRANSMEMBRANE CONDUCTANCE REGULATOR

(71) Applicant: Vertex Pharmaceuticals Incorporated, Cambridge, MA (US)

(72) Inventors: Xiaoqing Yang, San Diego, CA (US); Sara Sabina Hadida Ruah, La Jolla, CA (US); Peter Diederik Jan Grootenhuis, San Diego, CA (US); Fredrick F. Van Goor, San Diego, CA (US); Martyn Curtis Botfield, Concord, MA (US); Gregor Zlokarnik, La Jolla, CA (US)

(73) Assignee: Vertex Pharamaceuticals Incorporated, Boston, MA (US)

( * ) Notice: Subject to any disclaimer, the term of this patent is extended or adjusted under 35 U.S.C. 154(b) by 0 days.

(21) Appl. No.: 14/084,203

(22) Filed: Nov. 19, 2013

(65) Prior Publication Data

US 2014/0088142 A1 Mar. 27, 2014

Related U.S. Application Data

(60) Division of application No. 13/237,303, filed on Sep. 20, 2011, now Pat. No. 8,614,325, which is a continuation of application No. PCT/US2010/028062, filed on Mar. 19, 2010.

(60) Provisional application No. 61/162,130, filed on Mar. 20, 2009.

(51) Int. Cl.
*A61K 31/47* (2006.01)

(52) U.S. Cl.
USPC .......................................................... 514/312

(58) Field of Classification Search
None
See application file for complete search history.

(56) References Cited

FOREIGN PATENT DOCUMENTS

| WO | 9105783 A1 | 5/1991 |
|---|---|---|
| WO | 0040561 A1 | 7/2000 |
| WO | 2006002421 A2 | 1/2006 |
| WO | 2007075901 A2 | 7/2007 |
| WO | 2007079139 A2 | 7/2007 |
| WO | 2009036412 A1 | 3/2009 |

OTHER PUBLICATIONS

International Search Report for PCT/US2010/028062, dated May 27, 2010.
Silverman, Richard B., "The Organic Chemistry of Drug Design and Drug Action," Chapter 2: Drug Discover, Design, and Development, Academic Press, 1992, pp. 5-51.

*Primary Examiner* — Janet L Andres
*Assistant Examiner* — Timothy R Rozof
(74) *Attorney, Agent, or Firm* — Honigman Miller Schwartz and Cohn LLP; Christopher C. Forbes; Jonathan P. O'Brien

(57) ABSTRACT

This invention relates to a compound of Formula I:

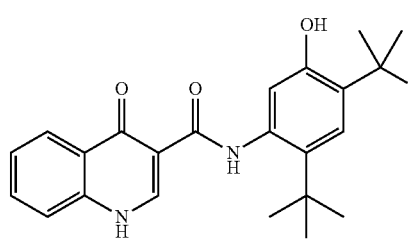

or a pharmaceutically acceptable salt thereof, wherein R is $COOH$ or $CH_2OH$.

4 Claims, No Drawings

MODULATORS OF CYSTIC FIBROSIS TRANSMEMBRANE CONDUCTANCE REGULATOR

CLAIM OF PRIORITY

This application is a divisional application of U.S. Ser. No. 13/237,303, filed on Sep. 20, 2011, which is a continuation of PCT Application No. PCT/US2010/028062 filed Mar. 19, 2010, which claims the priority of U.S. Application No. 61/162,130 filed Mar. 20, 2009. The entire contents of each of the aforementioned applications are incorporated herein by reference in their entirety.

TECHNICAL FIELD OF THE INVENTION

The present invention relates to modulators of cystic fibrosis transmembrane conductance regulator ("CFTR"), compositions thereof, and methods therewith. The present invention also relates to methods of treating diseases using modulators of CFTR.

BACKGROUND OF THE INVENTION

Cystic fibrosis (CF) is a recessive genetic disease that affects approximately 30,000 children and adults in the United States and approximately 30,000 children and adults in Europe. Despite progress in the treatment of CF, there is no cure.

CF is caused by mutations in the cystic fibrosis transmembrane conductance regulator (CFTR) gene that encodes an epithelial chloride ion channel responsible for aiding in the regulation of salt and water absorption and secretion in various tissues. Small molecule drugs, known as potentiators that increase the probability of CFTR channel opening represent one potential therapeutic strategy to treat CF.

Specifically, CFTR is a cAMP/ATP-mediated anion channel that is expressed in a variety of cells types, including absorptive and secretory epithelia cells, where it regulates anion flux across the membrane, as well as the activity of other ion channels and proteins. In epithelia cells, normal functioning of CFTR is critical for the maintenance of electrolyte transport throughout the body, including respiratory and digestive tissue. CFTR is composed of approximately 1480 amino acids that encode a protein made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

The gene encoding CFTR has been identified and sequenced (See Gregory, R. J. et al. (1990) Nature 347:382-386; Rich, D. P. et al. (1990) Nature 347:358-362), (Riordan, J. R. et al. (1989) Science 245:1066-1073). A defect in this gene causes mutations in CFTR resulting in cystic fibrosis ("CF"), the most common fatal genetic disease in humans. Cystic fibrosis affects approximately one in every 2,500 infants in the United States. Within the general United States population, up to 10 million people carry a single copy of the defective gene without apparent ill effects. In contrast, individuals with two copies of the CF associated gene suffer from the debilitating and fatal effects of CF, including chronic lung disease.

In patients with CF, mutations in CFTR endogenously expressed in respiratory epithelia leads to reduced apical anion secretion causing an imbalance in ion and fluid transport. The resulting decrease in anion transport contributes to enhanced mucus accumulation in the lung and the accompanying microbial infections that ultimately cause death in CF patients. In addition to respiratory disease, CF patients typically suffer from gastrointestinal problems and pancreatic insufficiency that, if left untreated, results in death. In addition, the majority of males with cystic fibrosis are infertile and fertility is decreased among females with cystic fibrosis. In contrast to the severe effects of two copies of the CF associated gene, individuals with a single copy of the CF associated gene exhibit increased resistance to cholera and to dehydration resulting from diarrhea—perhaps explaining the relatively high frequency of the CF gene within the population.

Sequence analysis of the CFTR gene of CF chromosomes has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, over 1000 disease causing mutations in the CF gene have been identified (http://www-.genet.sickkids.on.ca/cftr/app). The most prevalent mutation is a deletion of phenylalanine at position 508 of the CFTR amino acid sequence, and is commonly referred to as ΔF508-CFTR. This mutation occurs in approximately 70% of the cases of cystic fibrosis and is associated with a severe disease.

The deletion of residue 508 in ΔF508-CFTR prevents the nascent protein from folding correctly. This results in the inability of the mutant protein to exit the ER, and traffic to the plasma membrane. As a result, the number of channels present in the membrane is far less than observed in cells expressing wild-type CFTR. In addition to impaired trafficking, the mutation results in defective channel gating. Together, the reduced number of channels in the membrane and the defective gating lead to reduced anion transport across epithelia leading to defective ion and fluid transport. (Quinton, P. M. (1990), FASEB J. 4: 2709-2727). Studies have shown, however, that the reduced numbers of ΔF508-CFTR in the membrane are functional, albeit less than wild-type CFTR. (Dalemans et al. (1991), Nature Lond. 354: 526-528; Denning et al., supra; Pasyk and Foskett (1995), J. Cell. Biochem. 270: 12347-50). In addition to ΔF508-CFTR, other disease causing mutations in CFTR that result in defective trafficking, synthesis, and/or channel gating could be up- or down-regulated to alter anion secretion and modify disease progression and/or severity.

Although CFTR transports a variety of molecules in addition to anions, it is clear that this role (the transport of anions) represents one element in an important mechanism of transporting ions and water across the epithelium. The other elements include the epithelial $Na^+$ channel, ENaC, $Na^+/2Cl^-/K^+$ co-transporter, $Na^+$—$K^+$-ATPase pump and the basolateral membrane $K^+$ channels, that are responsible for the uptake of chloride into the cell.

These elements work together to achieve directional transport across the epithelium via their selective expression and localization within the cell. Chloride absorption takes place by the coordinated activity of ENaC and CFTR present on the apical membrane and the $Na^+$—$K^+$-ATPase pump and Cl ion channels expressed on the basolateral surface of the cell. Secondary active transport of chloride from the luminal side leads to the accumulation of intracellular chloride, which can then passively leave the cell via CF channels, resulting in a vectorial transport. Arrangement of $Na^+/2Cl^-/K^+$ co-transporter, $Na^+$—$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

As discussed above, it is believed that the deletion of residue 508 in ΔF508-CFTR prevents the nascent protein from folding correctly, resulting in the inability of this mutant protein to exit the ER, and traffic to the plasma membrane. As a result, insufficient amounts of the mature protein are present at the plasma membrane and chloride transport within epithelial tissues is significantly reduced. In fact, this cellular phenomenon of defective ER processing of ABC transporters by the ER machinery has been shown to be the underlying basis not only for CF disease, but for a wide range of other isolated and inherited diseases.

Accordingly, there is a need for modulators of CFTR activity, and compositions thereof, which can be used to modulate the activity of the CFTR in the cell membrane of a mammal.

There is a need for methods of treating diseases caused by mutation in CFTR using such modulators of CFTR activity.

There is a need for methods of modulating CFTR activity in an ex vivo cell membrane of a mammal.

SUMMARY OF THE INVENTION

In one aspect, this invention relates to a compound of Formula I:

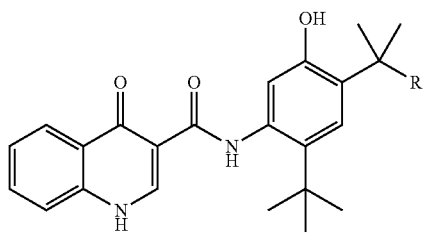

or a pharmaceutically acceptable salt thereof, wherein R is COOH or CH$_2$OH.

In one embodiment, the compound has the structure:

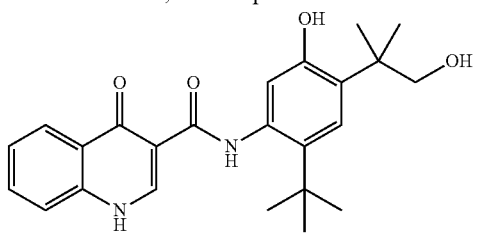

or a pharmaceutically acceptable salt thereof.

In another embodiment, the compound has the structure:

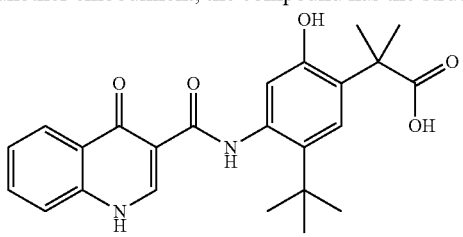

or a pharmaceutically acceptable salt thereof.

In one aspect, this invention relates to a pharmaceutical composition including a compound of Formula I, or a pharmaceutically acceptable salt thereof, wherein R is defined as above, and a pharmaceutically acceptable carrier or adjuvant.

In one embodiment of the pharmaceutical composition, the compound has the structure:

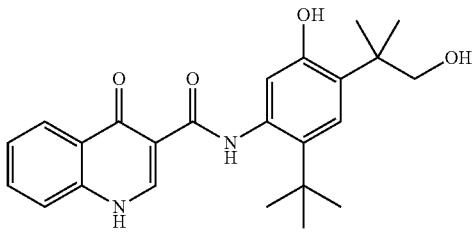 [SMILES: CC(C)(C)c1cc(C(C)(C)CO)c(O)cc1NC(=O)c1c[nH]c2ccccc2c1=O]

or a pharmaceutically acceptable salt thereof.

In another embodiment of the pharmaceutical composition, the compound has the structure:

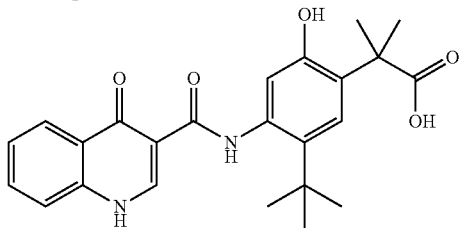 [SMILES: CC(C)(C)c1cc(C(C)(C)C(=O)O)c(O)cc1NC(=O)c1c[nH]c2ccccc2c1=O]

or a pharmaceutically acceptable salt thereof.

Embodiments of this aspect may also include a pharmaceutical composition containing an additional agent selected from a mucolytic agent, a bronchodilator, an antibiotic, an anti-infective agent, an anti-inflammatory agent, a CFTR modulator, or a nutritional agent.

In one aspect, this invention includes a method of modulating CFTR activity in a biological sample comprising the step of contacting said biological sample with a compound of Formula I, or a pharmaceutically acceptable salt thereof, wherein R is defined as above.

In one embodiment of the method of modulating CFTR activity, the compound has the structure:

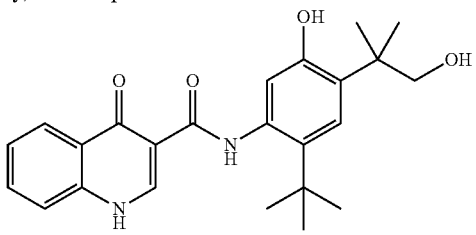

or a pharmaceutically acceptable salt thereof.

In another embodiment of the method of modulating CFTR activity, the compound has the structure:

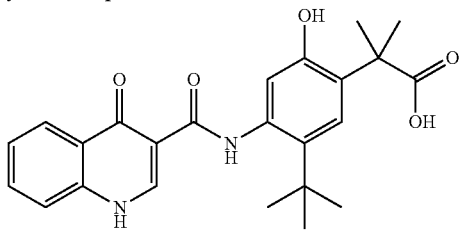

or a pharmaceutically acceptable salt thereof.

In another aspect, the invention also provides a method of treating or lessening the severity of a disease in a patient comprising administering to said patient one of the compositions as defined herein, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In another embodiment of the method of treating or lessening the severity of a disease, the disease is selected from CF, COPD, smoke induced COPD, pancreatitis, and rhinosinusitis.

In certain embodiments, the disease is cystic fibrosis.

In one embodiment of the method of treating or lessening the severity of a disease, the compound has the structure:

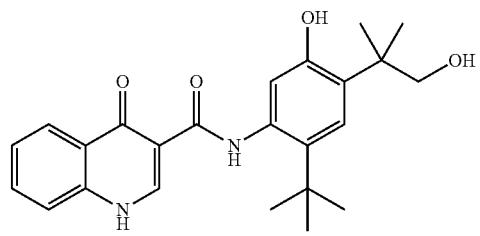 [SMILES: CC(C)(C)c1cc(C(C)(C)CO)c(O)cc1NC(=O)c1c[nH]c2ccccc2c1=O]

or a pharmaceutically acceptable salt thereof.

In another embodiment of the method of treating or lessening the severity of a disease, the compound has the structure:

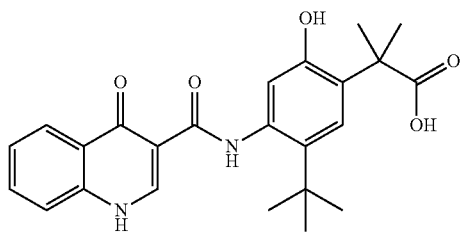 [SMILES: CC(C)(C)c1cc(C(C)(C)C(=O)O)c(O)cc1NC(=O)c1c[nH]c2ccccc2c1=O]

or a pharmaceutically acceptable salt thereof.

In another aspect, the present invention provides a kit for use in measuring the activity of CFTR or a fragment thereof in a biological sample in vitro or in vivo comprising (i) a composition comprising a compound of Formula I or any of the above embodiments; and (ii) instructions for a) contacting the composition with the biological sample and b) measuring activity of said CFTR or a fragment thereof.

In one embodiment of this aspect, the kit further comprises instructions for a) contacting an additional composition with the biological sample; b) measuring the activity of said CFTR or a fragment thereof in the presence of said additional compound, and c) comparing the activity of the CFTR or a fragment thereof in the presence of the additional compound with the density of the CFTR or a fragment thereof in the presence of a composition of Formula I.

In preferred embodiments, the kit is used to measure the density of CFTR or a fragment thereof.

In a further preferred embodiment, the kit is used to measure the density of said CFTR or a fragment thereof and the step of comparing the activity of said CFTR or a fragment thereof provides a measure of the density of said CFTR or a fragment thereof.

In one embodiment of the kit for use in measuring the activity of CFTR, the compound has the structure:

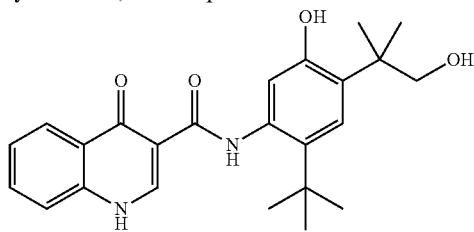

or a pharmaceutically acceptable salt thereof.

In another embodiment of the kit for use in measuring the activity of CFTR, the compound has the structure:

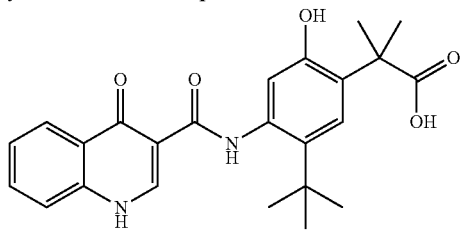

or a pharmaceutically acceptable salt thereof.

The compounds of Formula I provide advantageous properties such as, but not limited to, increased polarity, favorable aqueous solubility, lower distribution volume and lower tissue penetration.

DETAILED DESCRIPTION

Definitions

Compounds of this invention include those described generally above, and are further illustrated by the classes, subclasses, and species disclosed herein. As used herein, the following definitions shall apply unless otherwise indicated.

The term "ABC-transporter" as used herein means an ABC-transporter protein or a fragment thereof comprising at least one binding domain, wherein said protein or fragment thereof is present in vivo or in vitro. The term "binding domain" as used herein means a domain on the ABC-transporter that can bind to a modulator. See, e.g., Hwang, T. C. et al., J. Gen. Physiol. (1998): 111(3), 477-90.

The term "CFTR" as used herein means cystic fibrosis transmembrane conductance regulator or a mutation thereof capable of regulator activity, including, but not limited to, ΔF508 CFTR and G551D CFTR (see, e.g., http://www.genet.sickkids.on.ca/cftr/, for CFTR mutations).

The term "modulating" as used herein means increasing or decreasing by a measurable amount.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "protecting group" (PG) as used herein, represents those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups in Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are tert-butyloxycarbonyl (Boc).

Examples of useful protecting groups for acids are substituted alkyl esters such as 9-fluorenylmethyl, methoxymethyl, methylthiomethyl, tetrahydropyranyl, tetrahydropyranyl, methoxyethoxymethyl, 2-(trimethylsilyl)ethoxymethyl, benzyloxymethyl, pivaloyloxymethyl, phenylacetoxymethyl, triisopropropylsysilylmethyl, cyanomethyl, acetol, phenacyl, substituted phenacyl esters, 2,2,2-trichloroethyl, 2-haloethyl, ω-chloroalkyl, 2-(trimethylsilyl)ethyl, 2-methylthioethyl, t-butyl, 3-methyl-3-pentyl, dicyclopropylmethyl, cyclopentyl, cyclohexyl, allyl, methallyl, cynnamyl, phenyl, silyl esters, benzyl and substituted benzyl esters, 2,6-dialkylphenyl esters such as pentafluorophenyl, 2,6-dialkylpyhenyl. Preferred protecting groups for acids are methyl or ethyl esters.

Methods of adding (a process generally referred to as "protection") and removing (process generally referred to as "deprotection") such amine and acid protecting groups are well-known in the art and available, for example in P. J. Kocienski, Protecting Groups, Thieme, 1994, which is hereby incorporated by reference in its entirety and in Greene and Wuts, *Protective Groups in Organic Synthesis*, 3$^{rd}$ Edition (John Wiley & Sons, New York, 1999).

Unless otherwise stated, all tautomeric forms of the compounds of the invention are within the scope of the invention. That is, compounds of Formula I may exist as tautomers:

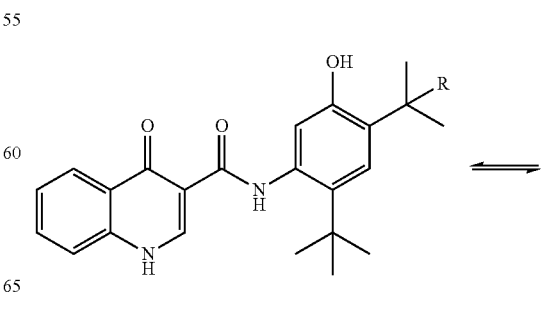

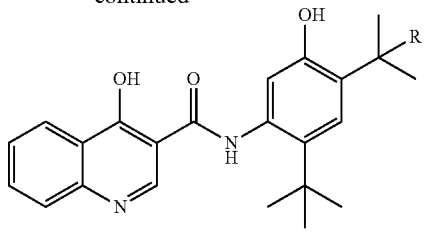

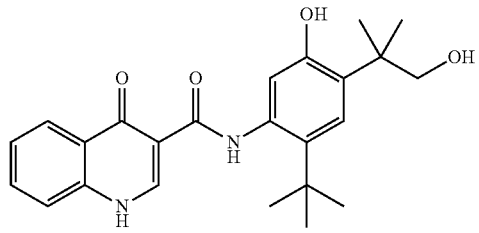 [SMILES: CC(C)(C)c1cc(C(C)(C)CO)c(O)cc1NC(=O)c1c[nH]c2ccccc2c1=O]

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools, probes in biological assays or as therapeutic agents.

Examples of suitable solvents are, but not limited to, water, methanol, dichloromethane (DCM), acetonitrile, dimethylformamide (DMF), ethyl acetate (EtOAc), isopropyl alcohol (IPA), isopropyl acetate (IPAc), tetrahydrofuran (THF), methyl ethyl ketone (MEK), t-butanol and N-methylpyrrolidone (NMP).

Examples of suitable coupling agents are, but not limited to, 1-(3-(dimethylamino)propyl)-3-ethyl-carbodiimide hydrochloride (EDCI), 2-(1H-benzotriazole-1-yl)-1,1,3,3-tetramethyluronium hexafluorophosphate (HBTU), 1-hydroxybenzotriazole (HOBT), 2-(1H-7-Azabenzotriazol-1-yl)-1,1,3,3-tetramethyl uronium hexafluorophosphate (HATU), 2-chloro-1,3-dimethyl-2-imidazolium tetrafluoroborate, 1-H-benzotriazolium-1-[bis(dimethylamino)methylene]-5-chlorohexafluorophosphate (HCTU), 2-chloro-4,6-dimethoxy-1,3,5-triazine, and 2-propane phosphonic anhydride (T3P®).

Examples of suitable bases are, but not limited to, $K_2CO_3$, N-Methylmorpholine (NMM), triethylamine (TEA), diisopropyl-ethyl amine (DIEA), pyridine, potassium hydroxide, sodium hydroxide, and sodium methoxide.

Compounds

In one embodiment, the invention includes a compound of Formula I:

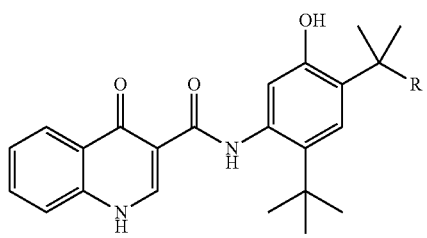

I or a pharmaceutically acceptable salt thereof, wherein R is COOH or $CH_2OH$.

In some embodiments, R is $CH_2OH$.

In some embodiments, R is COOH.

In another embodiment, the invention includes a compound of the structure:

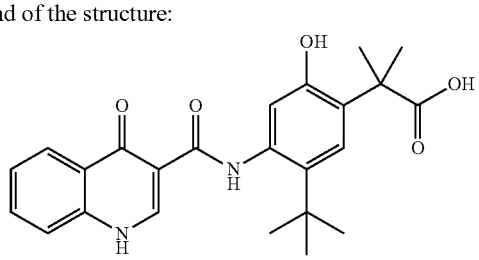

or a pharmaceutically acceptable salt thereof.

In another embodiment, the invention includes a compound of the structure:

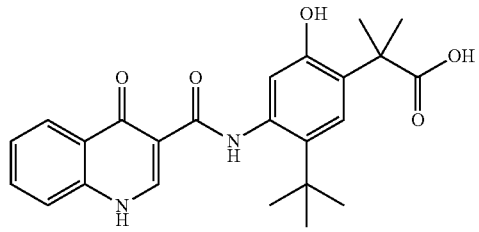 [SMILES: CC(C)(C)c1cc(C(C)(C)C(=O)O)c(O)cc1NC(=O)c1c[nH]c2ccccc2c1=O]

or a pharmaceutically acceptable salt thereof.

In one embodiment, the invention includes a pharmaceutical composition comprising a compound of Formula I, and a pharmaceutically acceptable carrier or adjuvant.

In another embodiment, the invention includes a pharmaceutical composition comprising a compound of the structure:

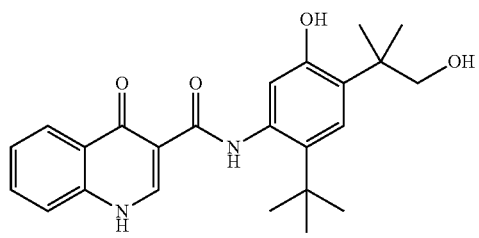 [SMILES: CC(C)(C)c1cc(C(C)(C)CO)c(O)cc1NC(=O)c1c[nH]c2ccccc2c1=O]

and a pharmaceutically acceptable carrier or adjuvant.

In another embodiment, the invention includes a pharmaceutical composition comprising a compound of the structure:

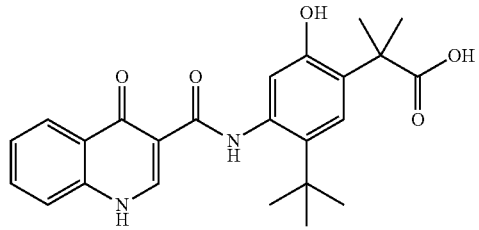 [SMILES: CC(C)(C)c1cc(C(C)(C)C(=O)O)c(O)cc1NC(=O)c1c[nH]c2ccccc2c1=O]

and a pharmaceutically acceptable carrier or adjuvant.

In a another embodiment, the pharmaceutical composition further comprises an additional agent selected from a mucolytic agent, a bronchodilator, an antibiotic, an anti-invective agent, an anti-inflammatory agent, a CFTR modulator, or a nutritional agent.

III. General Synthesis

Compounds of Formula I can be synthesized according to Scheme 1.

Scheme 1

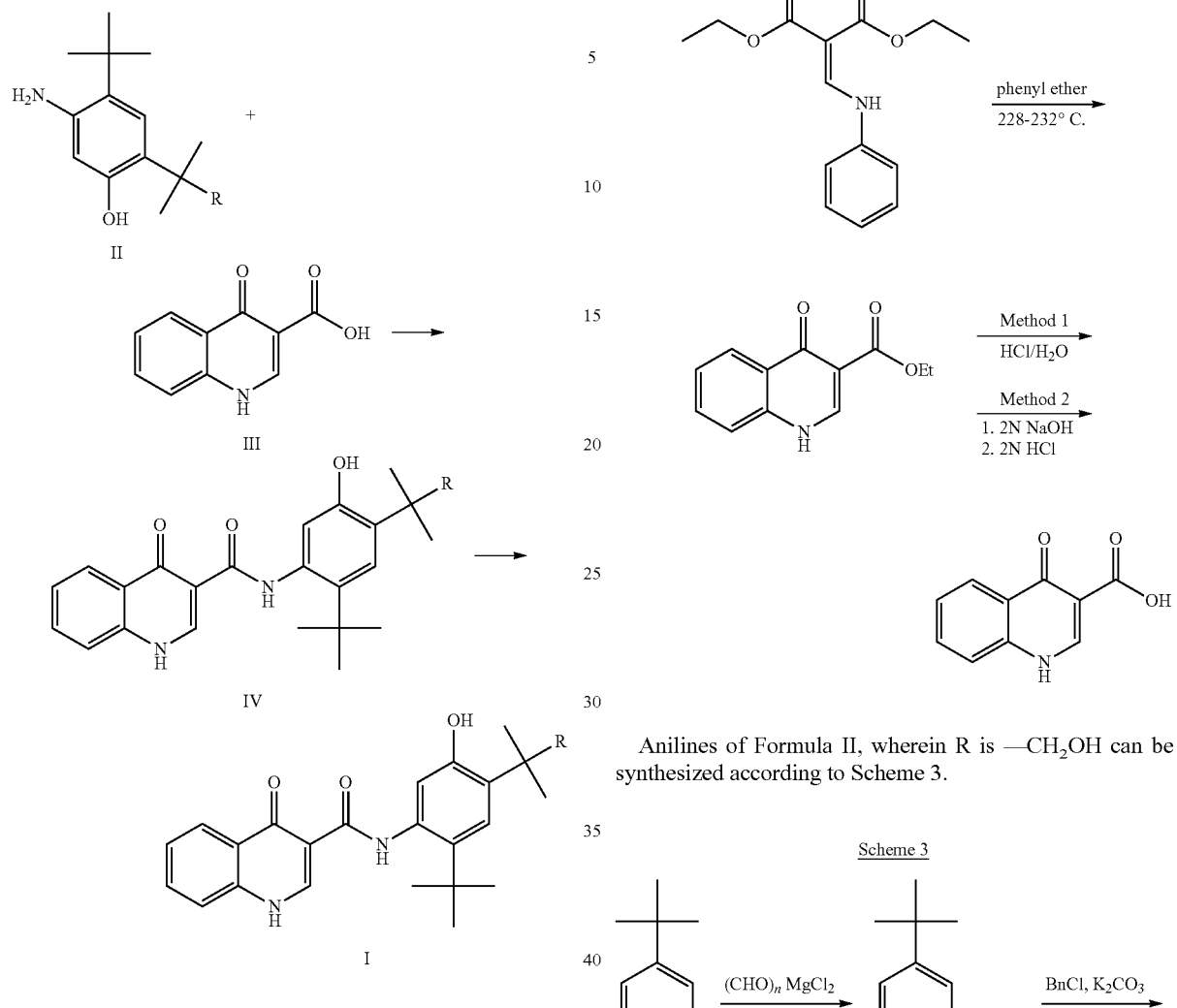

In Scheme 1, anilines of Formula II, wherein R and OH optionally and independently bear protecting groups thereon, are reacted with carboxylic acid intermediates of Formula III under coupling conditions to form compounds of Formula IV. Compounds of Formula IV that bear one or more protecting groups can then be deprotected to provide derivatives of Formula I.

The coupling reaction described in Scheme 1 can be achieved by dissolving the reactants in a suitable solvent, treating the resulting solution with a suitable coupling reagent optionally in the presence of a suitable base.

Quinoline derivatives of Formula III can be synthesized according to Scheme 2.

Scheme 2

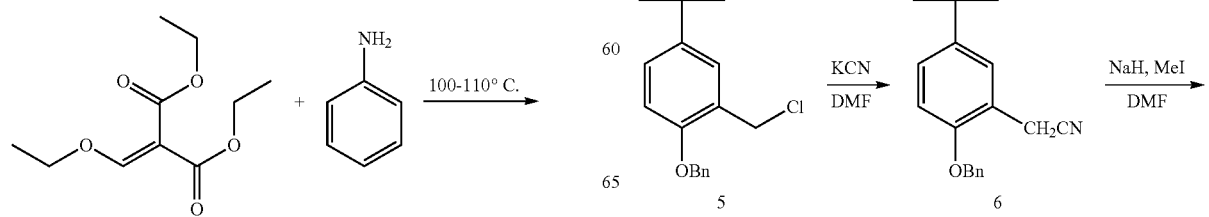

Anilines of Formula II, wherein R is —CH$_2$OH can be synthesized according to Scheme 3.

Scheme 3

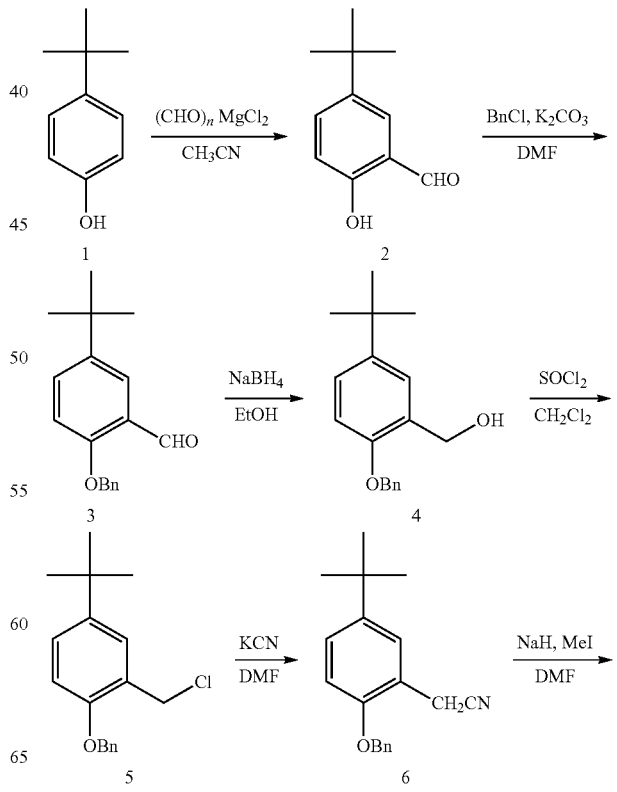

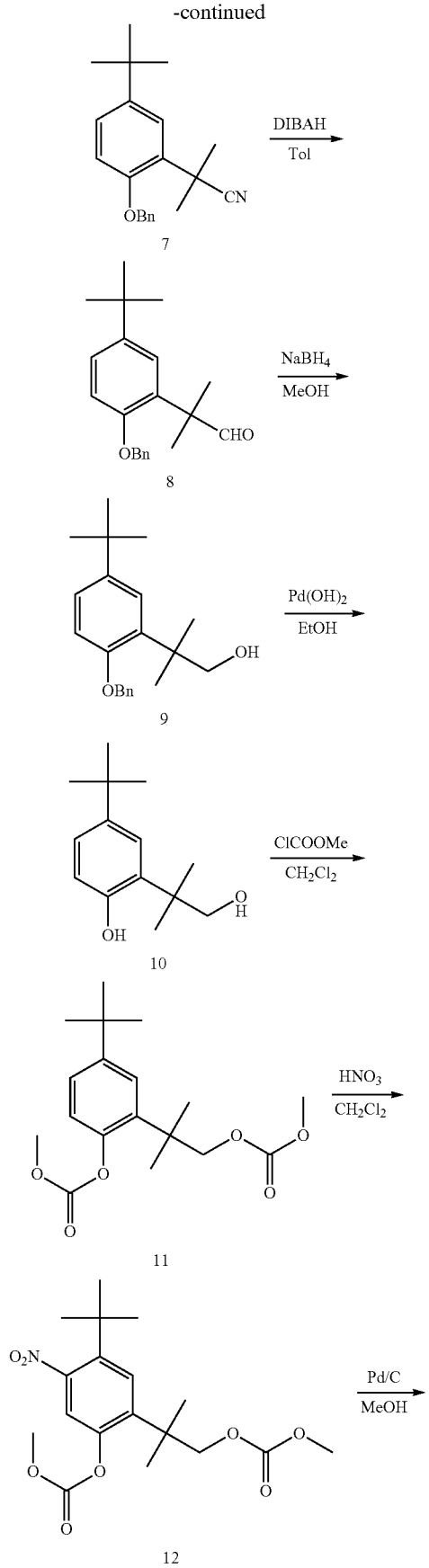
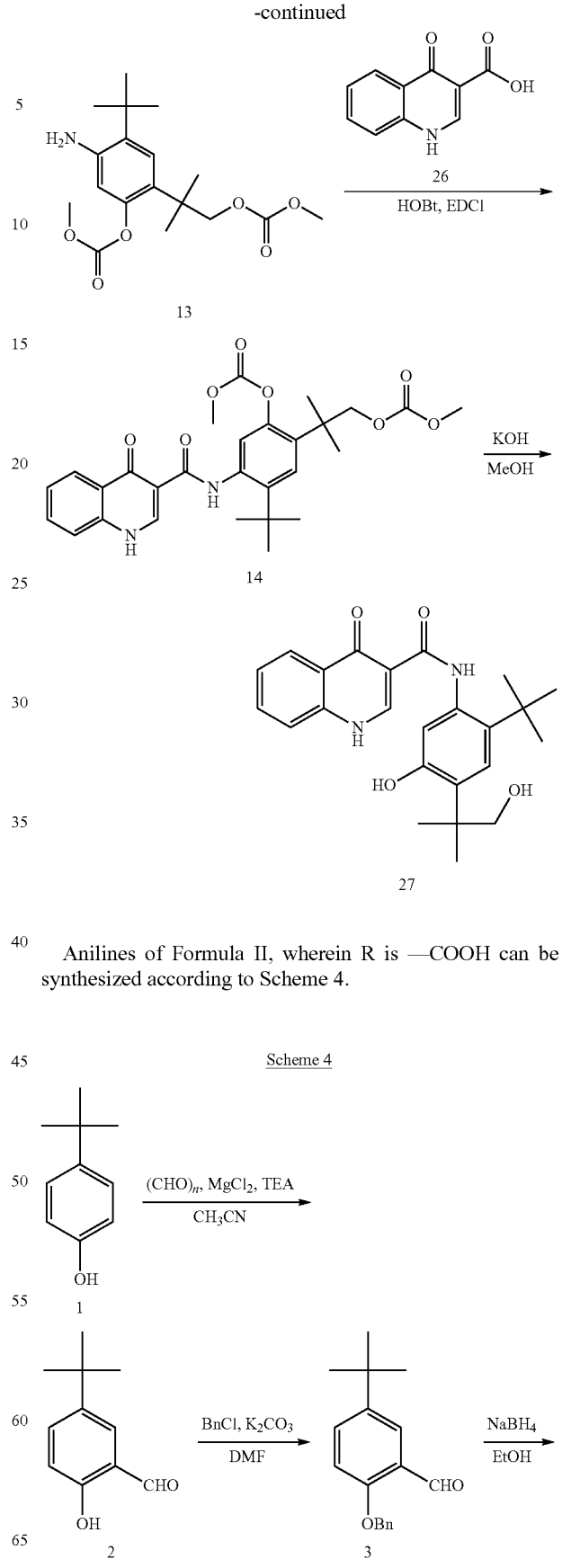
Anilines of Formula II, wherein R is —COOH can be synthesized according to Scheme 4.
Scheme 4

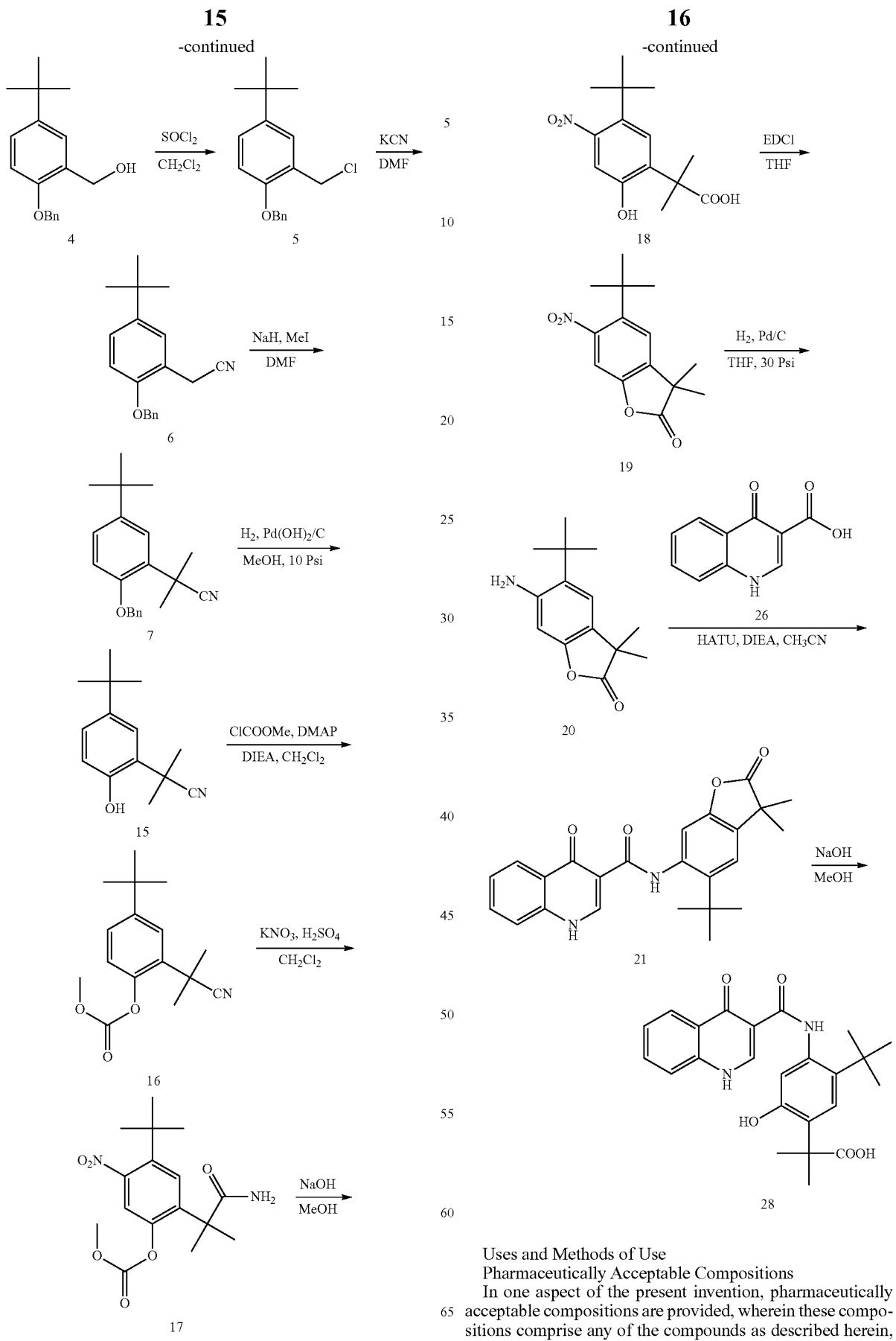
Uses and Methods of Use
Pharmaceutically Acceptable Compositions
In one aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a patient in need thereof is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, edisylate (ethanedisulfonate), ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, the present invention provides a method of treating, or lessening the severity of a condition, disease, or disorder implicated by CFTR mutation. In certain embodiments, the present invention provides a method of treating a condition, disease, or disorder implicated by a deficiency of the CFTR activity, the method comprising administering a composition comprising a compound of Formula I to a subject, preferably a mammal, in need thereof.

In another aspect, the invention also provides a method of treating or lessening the severity of a disease in a patient comprising administering to said patient one of the compositions as defined herein, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington's, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease, Osteoporosis, Osteopenia, bone healing and bone growth (including bone repair, bone regeneration, reducing bone resorption and increasing bone deposition), Gorham's Syndrome, chloride channelopathies such as myotonia congenita (Thomson and Becker forms), Bartter's syndrome type III, Dent's disease, hyperekplexia, epilepsy, hyperekplexia, lysosomal storage disease, Angelman syndrome, and Primary Ciliary Dyskinesia (PCD), a term for inherited disorders of the structure and/or function of cilia, including PCD with situs inversus (also known as Kartagener syndrome), PCD without situs inversus and ciliary aplasia.

In some embodiments, the method includes treating or lessening the severity of cystic fibrosis in a patient comprising administering to said patient one of the compositions as defined herein. In certain embodiments, the patient possesses mutant forms of human CFTR. In other embodiments, the patient possesses one or more of the following mutations ΔF508, R117H, and G551D of human CFTR. In one embodiment, the method includes treating or lessening the severity of cystic fibrosis in a patient possessing the ΔF508 mutation of human CFTR comprising administering to said patient one of the compositions as defined herein. In one embodiment, the method includes treating or lessening the severity of cystic fibrosis in a patient possessing the G551D mutation of human CFTR comprising administering to said patient one of the compositions as defined herein. In one embodiment, the method includes treating or lessening the severity of cystic fibrosis in a patient possessing the ΔF508 mutation of human CFTR on at least one allele comprising administering to said patient one of the compositions as defined herein. In one embodiment, the method includes treating or lessening the severity of cystic fibrosis in a patient possessing the ΔF508 mutation of human CFTR on both alleles comprising administering to said patient one of the compositions as defined herein. In one embodiment, the method includes treating or lessening the severity of cystic fibrosis in a patient possessing the G551D mutation of human CFTR on at least one allele comprising administering to said patient one of the compositions as defined herein. In one embodiment, the method includes treating or lessening the severity of cystic fibrosis in a patient possessing the G551D mutation of human CFTR on both alleles comprising administering to said patient one of the compositions as defined herein.

In some embodiments, the method includes lessening the severity of cystic fibrosis in a patient comprising administering to said patient one of the compositions as defined herein. In certain embodiments, the patient possesses mutant forms of human CFTR. In other embodiments, the patient possesses one or more of the following mutations ΔF508, R117H, and G551D of human CFTR. In one embodiment, the method includes lessening the severity of cystic fibrosis in a patient possessing the ΔF508 mutation of human CFTR comprising administering to said patient one of the compositions as defined herein. In one embodiment, the method includes lessening the severity of cystic fibrosis in a patient possessing the G551D mutation of human CFTR comprising administering to said patient one of the compositions as defined herein. In one embodiment, the method includes lessening the severity of cystic fibrosis in a patient possessing the ΔF508 mutation of human CFTR on at least one allele comprising administering to said patient one of the compositions as defined herein. In one embodiment, the method includes lessening the severity of cystic fibrosis in a patient possessing the ΔF508 mutation of human CFTR on both alleles comprising administering to said patient one of the compositions as defined herein. In one embodiment, the method includes lessening the severity of cystic fibrosis in a patient possessing the G551D mutation of human CFTR on at least one allele comprising administering to said patient one of the compositions as defined herein. In one embodiment, the method includes lessening the severity of cystic fibrosis in a patient possessing the G551D mutation of human CFTR on both alleles comprising administering to said patient one of the compositions as defined herein.

In some aspects, the invention provides a method of treating or lessening the severity of Osteoporosis in a patient comprising administering to said patient compound of Formula 1 or a pharmaceutically acceptable salt thereof.

In certain embodiments, the method of treating or lessening the severity of Osteoporosis in a patient comprises administering to said patient a pharmaceutical composition as described herein.

In some aspects, the invention provides a method of treating or lessening the severity of Osteopenia in a patient comprising administering to said patient compound of Formula 1 or a pharmaceutically acceptable salt thereof.

In certain embodiments, the method of treating or lessening the severity of Osteopenia in a patient comprises administering to said patient a pharmaceutical composition as described herein.

In some aspects, the invention provides a method of bone healing and/or bone repair in a patient comprising administering to said patient compound of Formula 1 or a pharmaceutically acceptable salt thereof.

In certain embodiments, the method of bone healing and/or bone repair in a patient comprises administering to said patient a pharmaceutical composition as described herein.

In some aspects, the invention provides a method of reducing bone resorption in a patient comprising administering to said patient compound of Formula 1 or a pharmaceutically acceptable salt thereof.

In some aspects, the invention provides a method of increasing bone deposition in a patient comprising administering to said patient compound of Formula 1 or a pharmaceutically acceptable salt thereof.

In certain embodiments, the method of increasing bone deposition in a patient comprises administering to said patient a pharmaceutical composition as described herein.

In some aspects, the invention provides a method of treating or lessening the severity of COPD in a patient comprising administering to said patient compound of Formula 1 or a pharmaceutically acceptable salt thereof.

In certain embodiments, the method of treating or lessening the severity of COPD in a patient comprises administering to said patient a pharmaceutical composition as described herein.

In some aspects, the invention provides a method of treating or lessening the severity of smoke induced COPD in a patient comprising administering to said patient compound of Formula 1 or a pharmaceutically acceptable salt thereof.

In certain embodiments, the method of treating or lessening the severity of smoke induced COPD in a patient comprises administering to said patient a pharmaceutical composition as described herein.

In some aspects, the invention provides a method of treating or lessening the severity of chronic bronchitis in a patient comprising administering to said patient compound of Formula 1 or a pharmaceutically acceptable salt thereof.

In certain embodiments, the method of treating or lessening the severity of chronic bronchitis in a patient comprises administering to said patient a pharmaceutical composition as described herein.

According to an alternative preferred embodiment, the present invention provides a method of treating cystic fibrosis comprising the step of administering to said mammal a composition comprising a compound of the present invention.

According to the invention an "effective amount" of the compound or pharmaceutically acceptable composition is that amount effective for treating or lessening the severity of one or more of the diseases, disorders or conditions as recited above.

Another aspect of the present invention provides a method of administering a pharmaceutical composition by orally administering to a patient at least once per day the composition comprising a compound of Formula 1. In one embodiment, the method comprises administering a pharmaceutical composition comprising a compound of Formula 1 every 24 hours. In another embodiment, the method comprises administering a pharmaceutical composition comprising a compound of Formula 1 every 12 hours. In a further embodiment, the method comprises administering a pharmaceutical composition comprising a compound of Formula 1 three times per day. In still a further embodiment, the method comprises administering a pharmaceutical composition comprising a compound of Formula 1 every 4 hours.

The compounds and compositions, according to the method of the present invention, may be administered using any amount and any route of administration effective for treating or lessening the severity of one or more of the diseases, disorders or conditions as recited above.

In certain embodiments, the compounds and compositions of the present invention are useful for treating or lessening the severity of cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary Cl⁻ concentrations, or ex vivo biochemical or histochemical techniques to monitor cell surface density. Using such methods, residual CFTR activity can be readily detected in patients heterozygous or homozygous for a variety of different mutations, including patients homozygous or heterozygous for the most common mutation, ΔF508.

In another embodiment, the compounds and compositions of the present invention are useful for treating or lessening the severity of cystic fibrosis in patients who have residual CFTR activity induced or augmented using pharmacological methods or gene therapy. Such methods increase the amount of CFTR present at the cell surface, thereby inducing a hitherto absent CFTR activity in a patient or augmenting the existing level of residual CFTR activity in a patient.

In one embodiment, the compounds and compositions of the present invention are useful for treating or lessening the severity of cystic fibrosis in patients within certain genotypes exhibiting residual CFTR activity, e.g., class III mutations (impaired regulation or gating), class IV mutations (altered conductance), or class V mutations (reduced synthesis) (Lee R. Choo-Kang, Pamela L., Zeitlin, *Type I, II, III, IV, and V cystic fibrosis Transmembrane Conductance Regulator Defects and Opportunities of Therapy*; Current Opinion in Pulmonary Medicine 6:521-529, 2000). Other patient genotypes that exhibit residual CFTR activity include patients homozygous for one of these classes or heterozygous with any other class of mutations, including class I mutations, class II mutations, or a mutation that lacks classification.

In one embodiment, the compounds and compositions of the present invention are useful for treating or lessening the severity of cystic fibrosis in patients within certain clinical phenotypes, e.g., a moderate to mild clinical phenotype that typically correlates with the amount of residual CFTR activity in the apical membrane of epithelia. Such phenotypes include patients exhibiting pancreatic insufficiency or patients diagnosed with idiopathic pancreatitis and congenital bilateral absence of the vas deferens, or mild lung disease.

The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The activity of a compound utilized in this invention as a modulator of CFTR may be assayed according to methods described generally in the art and in the Examples herein.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated."

In one embodiment, the additional agent is selected from a mucolytic agent, bronchodialator, an anti-biotic, an anti-infective agent, an anti-inflammatory agent, a CFTR modulator other than a compound of the present invention, or a nutritional agent.

In one embodiment, the additional agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In another embodiment, the additional agent is a mucolyte. Exemplary mucolytes useful herein includes Pulmozyme®.

In another embodiment, the additional agent is a bronchodialator. Exemplary bronchodilators include albuterol, metaprotenerol sulfate, pirbuterol acetate, salmeterol, or tetrabuline sulfate.

In another embodiment, the additional agent is effective in restoring lung airway surface liquid. Such agents improve the movement of salt in and out of cells, allowing mucus in the lung airway to be more hydrated and, therefore, cleared more easily. Exemplary such agents include hypertonic saline, denufosol tetrasodium ([[(3S, 5R)-5-(4-amino-2-oxopyrimidin-1-yl)-3-hydroxyoxolan-2-yl]methoxy-hydroxyphosphoryl][[[(2R,3S,4R,5R)-5-(2,4-dioxopyrimidin-1-yl)-3,4-dihydroxyoxolan-2-yl]methoxy-hydroxyphosphoryl]oxy-hydroxyphosphoryl]hydrogen phosphate), or bronchitol (inhaled formulation of mannitol).

In another embodiment, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In another embodiment, the additional agent is a CFTR modulator other than compound 1, i.e., an agent that has the effect of modulating CFTR activity. Exemplary such agents include ataluren ("PTC124®"; 3-[5-(2-fluorophenyl)-1,2,4-oxadiazol-3-yl]benzoic acid), sinapultide, lancovutide, depelestat (a human recombinant neutrophil elastase inhibitor), cobiprostone (7-{(2R,4aR,5R,7aR)-2-[(3S)-1,1-difluoro-3-methylpentyl]-2-hydroxy-6-oxooctahydrocyclopenta[b]pyran-5-yl}heptanoic acid), or (3-(6-(1-(2,2-difluorobenzo[d][1,3]dioxol-5-yl)cyclopropanecarboxamido)-3-methylpyridin-2-yl)benzoic acid. In another embodiment, the additional agent is (3-(6-(1-(2,2-difluorobenzo[d][1,3]dioxol-5-yl)cyclopropanecarboxamido)-3-methylpyridin-2-yl)benzoic acid.

In another embodiment, the additional agent is a nutritional agent. Exemplary such agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to modulating CFTR activity in a biological sample or a patient (e.g., in vitro or in vivo), which method comprises administering to the patient, or contacting said biological sample with a compound of Formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of CFTR in a biological sample is useful for a variety of purposes that are known to one of skill in the art. Examples of such purposes include, but are not limited to, the study of CFTR in biological and pathological phenomena; and the comparative evaluation of new modulators of CFTR.

In yet another embodiment, a method of modulating activity of an anion channel in vitro or in vivo, is provided comprising the step of contacting said channel with a compound of Formula I. In preferred embodiments, the anion channel is a chloride channel or a bicarbonate channel. In other preferred embodiments, the anion channel is a chloride channel.

According to an alternative embodiment, the present invention provides a method of increasing the number of functional CFTR in a membrane of a cell, comprising the step of contacting said cell with a compound of Formula I.

According to another preferred embodiment, the activity of the CFTR is measured by measuring the transmembrane voltage potential. Means for measuring the voltage potential across a membrane in the biological sample may employ any of the known methods in the art, such as optical membrane potential assay or other electrophysiological methods.

The optical membrane potential assay utilizes voltage-sensitive FRET sensors described by Gonzalez and Tsien (See Gonzalez, J. E. and R. Y. Tsien (1995) "Voltage sensing by fluorescence resonance energy transfer in single cells." *Biophys J* 69(4): 1272-80, and Gonzalez, J. E. and R. Y. Tsien (1997); "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR) (See Gonzalez, J. E., K. Oades, et al. (1999) "Cell-based assays and instrumentation for screening ion-channel targets" *Drug Discov Today* 4(9): 431-439).

These voltage sensitive assays are based on the change in fluorescence resonant energy transfer (FRET) between the membrane-soluble, voltage-sensitive dye, $DiSBAC_2(3)$, and a fluorescent phospholipid, CC2-DMPE, which is attached to the outer leaflet of the plasma membrane and acts as a FRET donor. Changes in membrane potential ($V_m$) cause the negatively charged $DiSBAC_2(3)$ to redistribute across the plasma membrane and the amount of energy transfer from CC2-DMPE changes accordingly. The changes in fluorescence emission can be monitored using VIPR™ II, which is an integrated liquid handler and fluorescent detector designed to conduct cell-based screens in 96- or 384-well microtiter plates.

In one embodiment, the present invention provides a method of modulating CFTR activity in a biological sample comprising the step of contacting said biological sample with a compound of Formula I, or a pharmaceutically acceptable salt thereof, wherein R is defined as above.

In one embodiment, the present invention provides a method of modulating CFTR activity in a biological sample comprising the step of contacting said biological sample with a compound of the structure:

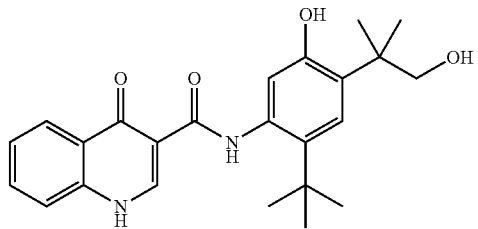 [SMILES: CC(C)(C)c1cc(C(C)(C)CO)c(O)cc1NC(=O)c1c[nH]c2ccccc2c1=O]

or a pharmaceutically acceptable salt thereof.

In one embodiment, the present invention provides a method of modulating CFTR activity in a biological sample comprising the step of contacting said biological sample with a compound of the structure:

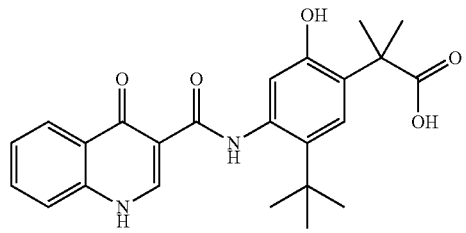 [SMILES: CC(C)(C)c1cc(C(C)(C)C(=O)O)c(O)cc1NC(=O)c1c[nH]c2ccccc2c1=O]

or a pharmaceutically acceptable salt thereof.

In one embodiment, the present invention provides a method of treating or lessening the severity of a disease in a patient comprising administering to said patient an effective amount of a compound of Formula I, or a pharmaceutically acceptable salt thereof, wherein R is defined as above, and said disease is selected from cystic fibrosis, asthma, smoke induced COPD, chronic bronchitis, rhinosinusitis, constipation, pancreatitis, pancreatic insufficiency, male infertility caused by congenital bilateral absence of the vas deferens (CBAVD), mild pulmonary disease, idiopathic pancreatitis, allergic bronchopulmonary aspergillosis (ABPA), liver disease, hereditary emphysema, hereditary hemochromatosis, coagulation-fibrinolysis deficiencies, such as protein C deficiency, Type 1 hereditary angioedema, lipid processing deficiencies, such as familial hypercholesterolemia, Type 1 chylomicronemia, abetalipoproteinemia, lysosomal storage diseases, such as I-cell disease/pseudo-Hurler, mucopolysaccharidoses, Sandhof/Tay-Sachs, Crigler-Najjar type II, polyendocrinopathy/hyperinsulemia, Diabetes mellitus, Laron dwarfism, myleoperoxidase deficiency, primary hypoparathyroidism, melanoma, glycanosis CDG type 1, congenital hyperthyroidism, osteogenesis imperfecta, hereditary hypofibrinogenemia, ACT deficiency, Diabetes insipidus (DI), neurophyseal DI, neprogenic DI, Charcot-Marie Tooth syndrome, Perlizaeus-Merzbacher disease, neurodegenerative diseases such as Alzheimer's disease, Parkinson's disease, amyotrophic lateral sclerosis, progressive supranuclear plasy, Pick's disease, several polyglutamine neurological disorders such as Huntington, spinocerebullar ataxia type I, spinal and bulbar muscular atrophy, dentatorubal pallidoluysian, and myotonic dystrophy, as well as spongiform encephalopathies, such as hereditary Creutzfeldt-Jakob disease (due to prion protein processing defect), Fabry disease, Straussler-Scheinker syndrome, COPD, dry-eye disease, or Sjogren's disease.

In one embodiment, the method includes treating or lessening the severity of a disease in a patient by administering to said patient an effective amount of a compound having the structure:

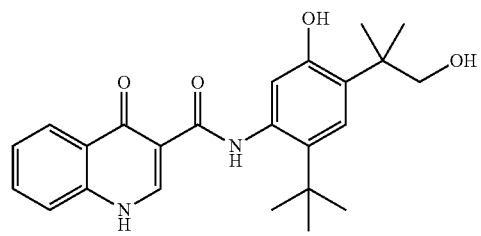 [SMILES: CC(C)(C)c1cc(C(C)(C)CO)c(O)cc1NC(=O)c1c[nH]c2ccccc2c1=O]

or a pharmaceutically acceptable salt thereof.

In another embodiment, the method includes treating or lessening the severity of a disease in a patient by administering to said patient an effective amount of a compound having the structure:

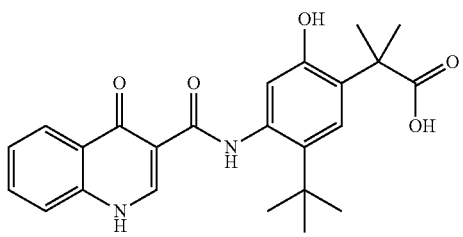 [SMILES: CC(C)(C)c1cc(C(C)(C)C(=O)O)c(O)cc1NC(=O)c1c[nH]c2ccccc2c1=O]

or a pharmaceutically acceptable salt thereof.

In one further embodiment, the disease is cystic fibrosis.

In another aspect the present invention provides a kit for use in measuring the activity of CFTR or a fragment thereof in a biological sample in vitro or in vivo comprising (i) a composition comprising a compound of Formula I or any of the above embodiments; and (ii) instructions for a) contacting the composition with the biological sample and b) measuring activity of said CFTR or a fragment thereof.

In one embodiment, the kit further comprises instructions for a) contacting an additional composition with the biological sample; b) measuring the activity of said CFTR or a fragment thereof in the presence of said additional compound, and c) comparing the activity of the CFTR in the presence of the additional compound with the density of the CFTR in the presence of a composition of Formula I.

In preferred embodiments, the kit is used to measure the density of CFTR.

In one embodiment, the kit includes a composition comprising a compound having the structure:

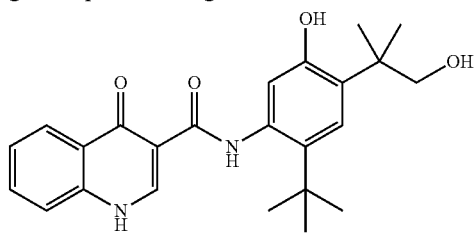

or a pharmaceutically acceptable salt thereof.

In one embodiment, the kit includes a composition comprising a compound having the structure:

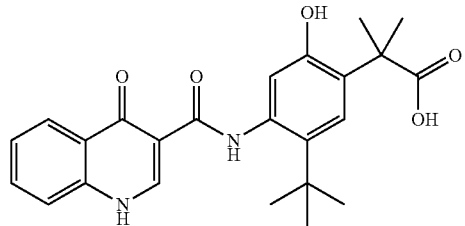 [SMILES: CC(C)(C)c1cc(C(C)(C)C(=O)O)c(O)cc1NC(=O)c1c[nH]c2ccccc2c1=O]

or a pharmaceutically acceptable salt thereof.

In order that the invention described herein may be more fully understood, the following examples are set forth. It should be understood that these examples are for illustrative purposes only and are not to be construed as limiting this invention in any manner.

EXAMPLES

Preparation 1

Total Synthesis of
4-oxo-1,4-dihydroquinoline-3-carboxylic acid (26)

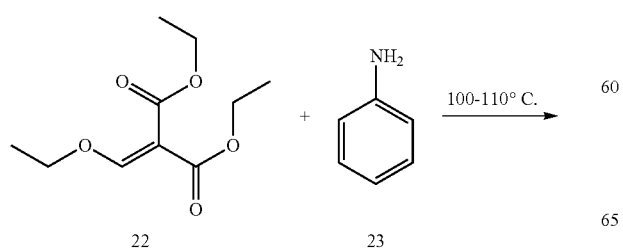

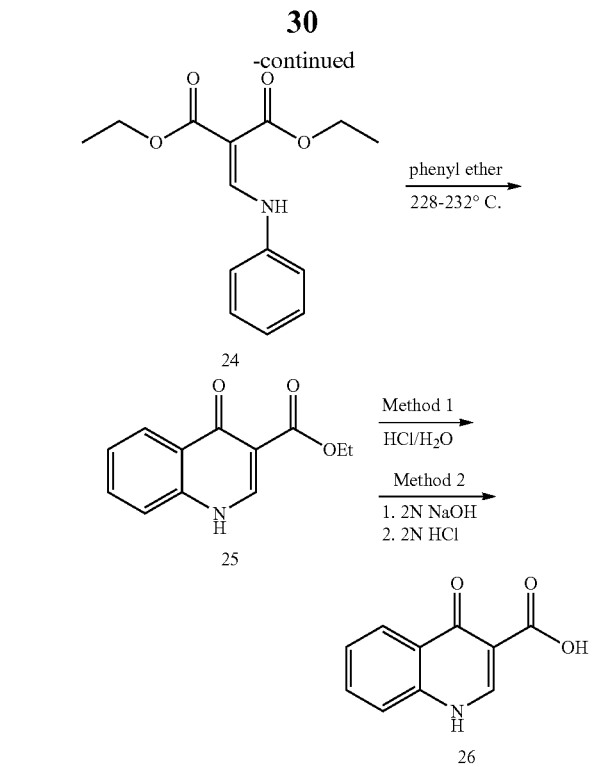

Procedure for the Preparation of Ethyl
4-Oxo-1,4-Dihydroquinoline-3-Carboxylate (25)

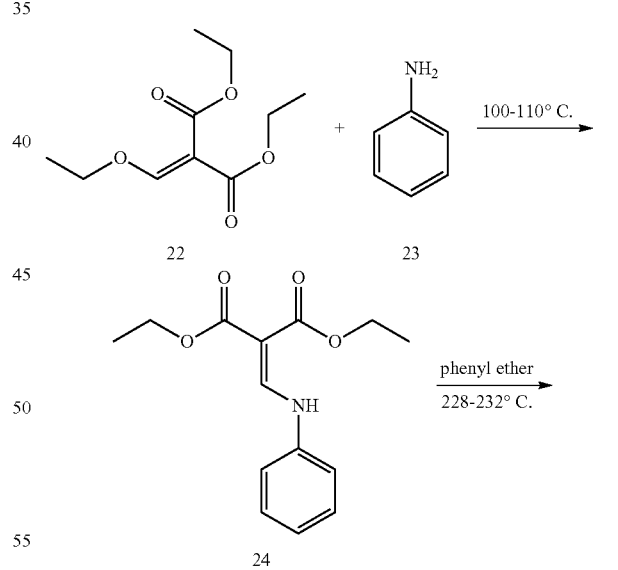

Compound 23 (4.77 g, 47.7 mmol) was added dropwise to compound 22 (10 g, 46.3 mmol) with subsurface $N_2$ flow to drive out ethanol below 30° C. for 0.5 hours. The solution was then heated to 100-110° C. and stirred for 2.5 hours. After cooling the mixture to below 60° C., diphenyl ether was added. The resulting solution was added dropwise to diphenyl ether that had been heated to 228-232° C. for 1.5 hours with subsurface $N_2$ flow to drive out ethanol. The mixture was stirred at 228-232° C. for another 2 hours, cooled to below 100° C. and then heptane was added to precipitate the product. The resulting slurry was stirred at 30° C. for 0.5 hours. The solids were then filtrated, and the cake was washed with heptane and dried in vacuo to give compound 25 as brown solid. $^1$H NMR (DMSO-$d_6$; 400 MHz) δ 12.25 (s), δ 8.49 (d), δ 8.10 (m), δ 7.64 (m), δ 7.55 (m), δ 7.34 (m), δ 4.16 (q), δ 1.23 (t).

Procedure for the Preparation of
4-Oxo-1,4-Dihydroquinoline-3-Carboxylic Acid (26)

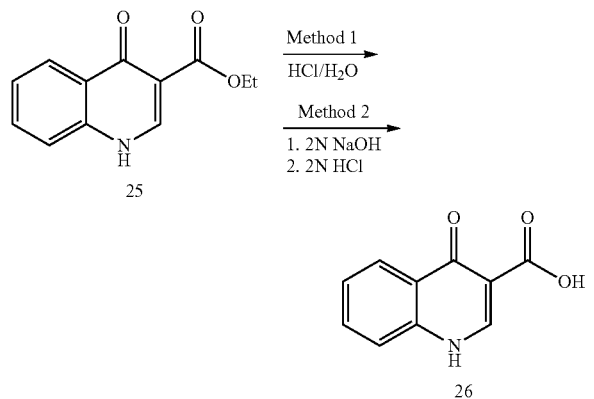

Method 1

Compound 25 (1.0 eq) was suspended in a solution of HCl (10.0 eq) and $H_2O$ (11.6 vol). The slurry was heated to 85-90° C., although alternative temperatures are also suitable for this hydrolysis step. For example, the hydrolysis can alternatively be performed at a temperature of from about 75 to about 100° C. In some instances, the hydrolysis is performed at a temperature of from about 80 to about 95° C. In others, the hydrolysis step is performed at a temperature of from about 82 to about 93° C. (e.g., from about 82.5 to about 92.5° C. or from about 86 to about 89° C.). After stirring at 85-90° C. for approximately 6.5 hours, the reaction was sampled for reaction completion. Stirring may be performed under any of the temperatures suited for the hydrolysis. The solution was then cooled to 20-25° C. and filtered. The reactor/cake was rinsed with $H_2O$ (2 vol×2). The cake was then washed with 2 vol $H_2O$ until the pH≥3.0. The cake was then dried under vacuum at 60° C. to give compound 26.

Method 2

Compound 25 (11.3 g, 52 mmol) was added to a mixture of 10% NaOH (aq) (10 mL) and ethanol (100 mL). The solution was heated to reflux for 16 hours, cooled to 20-25° C. and then the pH was adjusted to 2-3 with 8% HCl. The mixture was then stirred for 0.5 hours and filtered. The cake was washed with water (50 mL) and then dried in vacuo to give compound 26 as a brown solid. $^1$H NMR (DMSO-$d_6$; 400 MHz) δ 15.33 (s), δ 13.39 (s), δ 8.87 (s), δ 8.26 (m), δ 7.87 (m), δ 7.80 (m), δ 7.56 (m).

Example 1

Total synthesis of N-(2-tert-butyl-5-hydroxy-4-(1-hydroxy-2-methylpropan-2-yl)phenyl)-4-oxo-1,4-dihydroquinoline-3-carboxamide (27)

The overall scheme of the synthesis of compound 27 is shown below, followed by the procedure for the synthesis of each synthetic intermediate.

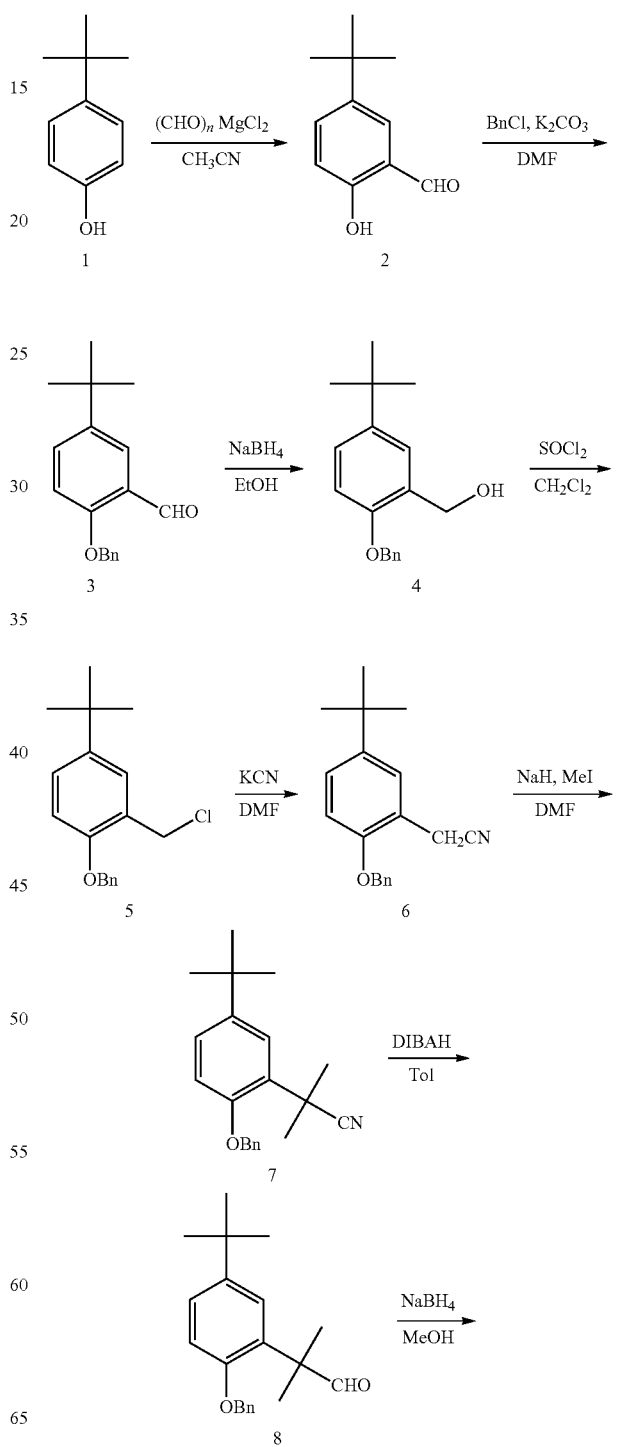

-continued

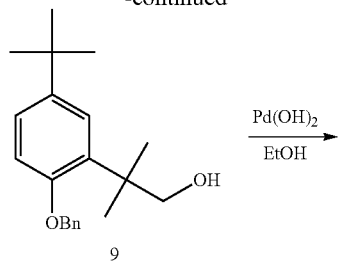

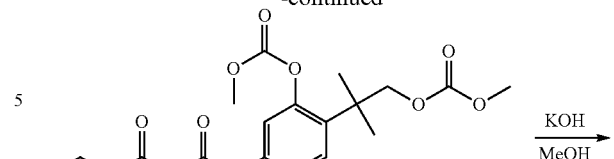

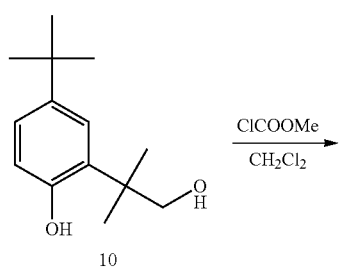

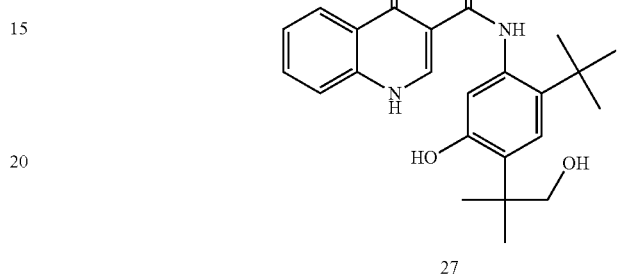

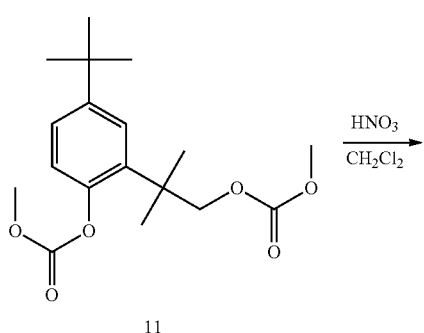

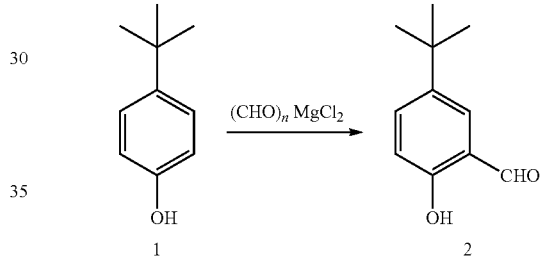

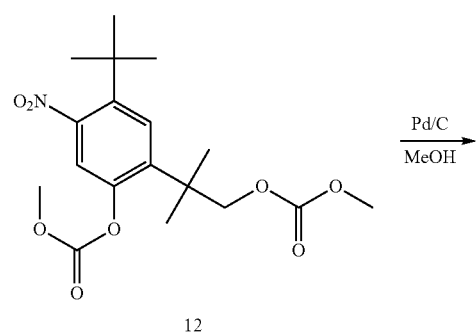

Procedure for the preparation of 2-hydroxy-5-tert-butylbenzaldehyde (2)

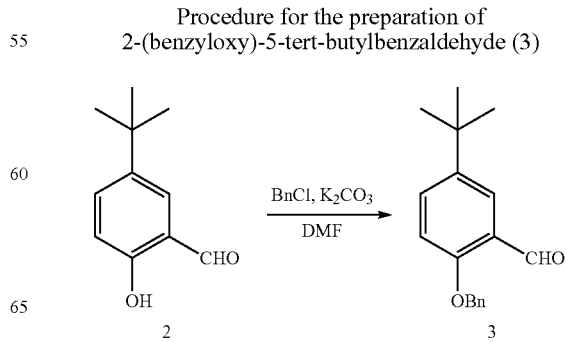

To a stirred solution of compound 1 (700 g, 4.66 mol) in CH$_3$CN (7.0 L) was added MgCl$_2$ (887 g, 9.32 mol), Para-Formaldehyde (1190 g) and TEA (2.5 L, 17.9 mol) under N$_2$. The mixture was heated to reflux for 5 hours. After cooling to room temperature, 2 L ice water was added to the mixture, followed by 6 L of 3 M HCl (aq). The suspension was left stirring until the solution became clear. The organic layer was separated and the aqueous layer was extracted with MTBE (3 L×3). The organic layers were combined and concentrated to dryness. The residue was dissolved in MTBE (4000 mL), washed with water (1000 mL×2) and brine (1000 mL), dried over anhydrous Na$_2$SO$_4$, filtered, then concentrated to give compound 2 as a light-yellow solid which was used in the next reaction without further drying or purification. $^1$H NMR (CDCl$_3$; 400 MHz) δ 10.86 (s), δ 9.89 (s), δ 7.59 (m), δ 7.51 (d), δ 6.94 (d), δ 10.61 (s).

Procedure for the preparation of 2-(benzyloxy)-5-tert-butylbenzaldehyde (3)

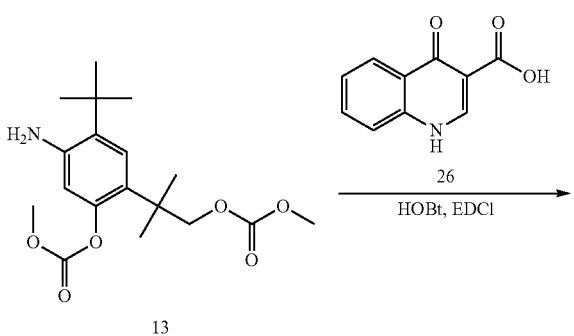

To a stirred solution of compound 2 (614.5 g, 3.33 mol) in DMF (3.5 L) was added K$_2$CO$_3$ (953 g, 6.90 mol) and benzyl chloride (480 g, 3.80 mol). The mixture was heated to 90° C. and left stirring for 3 hours. The suspension was cooled to room temperature, then MTBE (2 L) was added, followed by water (12 L). The mixture was then stirred for 10 minutes and the aqueous layer was separated and extracted with MTBE (2 L×3). The organic layers were combined and washed with water (2 L×2) and brine (1.5 L×1) and concentrated to give compound 3 as a light-yellow solid. $^1$H NMR (DMSO-d$_6$; 400 MHz) δ 10.42 (s), δ 7.71 (m), δ 7.51 (m), δ 7.43 (m), δ 7.35 (m), δ 7.24 (m), δ 5.27 (s), δ 1.26 (s).

Procedure for the preparation of
2-(benzyloxy)-5-tert-butylbenzyl alcohol (4)

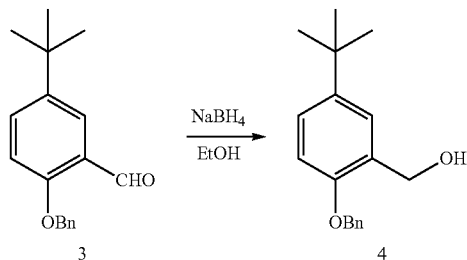 [SMILES: "EtOH" ; CC(C)(C)c1ccc(OCc2ccccc2)c(C=O)c1 ; "NaBH4" ; CC(C)(C)c1ccc(OCc2ccccc2)c(CO)c1]

To a stirred suspension of compound 3 (974 g, 3.63 mol) in MeOH (4000 mL) was slowly added NaBH$_4$ (121 g, 3.20 mol) at 0-20° C. The solution was left stirring at 15° C. for 3 hours, and then cooled to 0° C. 2N HCl (aq) (1300 mL) was added dropwise at below 20° C. The solution was then filtered and evaporated to dryness, and the residue was dissolved in MTBE (5 L). The solution was then washed with water (2 L×2) and brine (1.5 L×1). Evaporation of the solvent gave compound 4 as a light-yellow solid which was used in the next reaction without further purification. $^1$H NMR (DMSO-d$_6$; 400 MHz) δ 7.40 (m), δ 7.32 (m), δ 7.17 (m), δ 6.91 (m), δ 5.09 (s), δ 5.00 (t), δ 4.56 (d), δ 1.26 (s).

Procedure for the preparation of
2-(benzyloxy)-5-tert-butylbenzyl chloride (5)

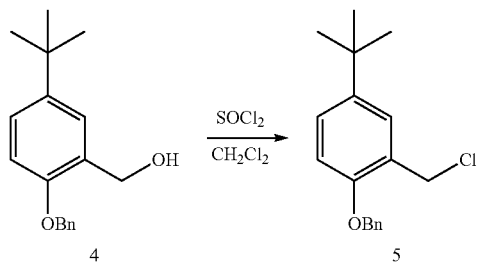

To a stirred solution of compound 4 (963 g, 3.56 mol) in anhydrous DCM (2000 mL) was added slowly SOCl$_2$ (535 g, 4.5 mol) at 0° C. The mixture was stirred at 20° C. for 2 hours, then concentrated in vacuo to give compound 5 as an oil, which was used in the next reaction without further drying or purification.

Procedure for the preparation of
2-(benzyloxy)-5-tert-butylbenzyl nitrile (6)

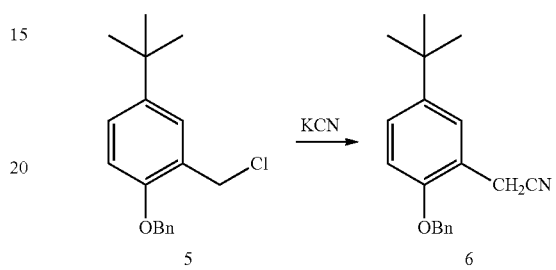

To a stirred solution of compound 5 (1045 g, 3.54 mol) in anhydrous DMF (1000 mL) was added KCN (733 g, 11.3 mol). The mixture was stirred at 35° C. for 24 hours, then poured into water (10 L). Ethyl acetate (4 L) was added and the mixture was stirred for 30 minutes. The organic layer was then separated and the aqueous layer was extracted with ethyl acetate (3000 mL×2). The organic layers were combined and washed with water (4 L×2) and brine (3 L×1), then concentrated in vacuo to give compound 6 as a yellow solid. $^1$H NMR (DMSO-d$_6$; 400 MHz) δ 7.51 (m), δ 7.37 (m), 7.02 (d), δ 5.17 (s), δ 3.88 (s), 1.26 (s).

Procedure for the preparation of 2-(2-(benzyloxy)-5-tert-butylphenyl)-2-methylpropanenitrile (7)

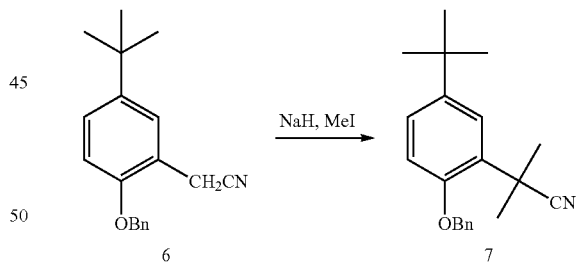

To a stirred suspension of NaH (86 g, 2.15 mol, 60% in mineral oil) in DMF (1000 mL) was added dropwise a solution of compound 6 (100.0 g, 0.358 mol) in DMF (500 mL) at 20° C. After stirring for 30 minutes, MeI (205 g, 1.44 mol) in DMF (500 mL) was added dropwise at below 30° C. during a period of 2 hours. The suspension was stirred for 1.5 hours at 25-30° C., then ice (100 g) was added slowly until no gas was generated. The pH was adjusted to approximately 7 by the slow addition of 2N HCl. The mixture was diluted with water (4 L) and MTBE (2 L). The organic layer was separated and the aqueous layer was extracted with MTBE (500 mL×2). The combined organic layers were washed with water and brine, dried over Na$_2$SO$_4$, filtered, and then concentrated in vacuo to give compound 7 as a white solid. $^1$H NMR (DMSO-d$_6$; 400 MHz) δ 7.56 (m), δ 7.40 (m), δ 7.34 (m), δ 7.10 (d), δ 5.21 (s), δ 1.73 (s), δ 1.27 (s).

Procedure for the preparation of 2-(2-(benzyloxy)-5-tert-butylphenyl)-2-methylpropanal (8)

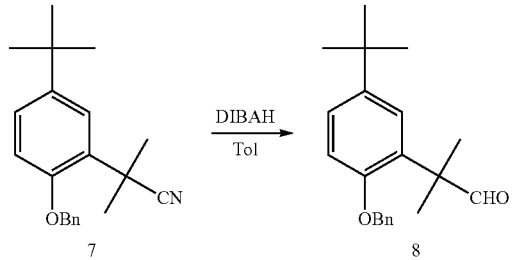 [SMILES: CC(C)(C)c1ccc(OCc2ccccc2)c(C(C)(C)C#N)c1 ; "DIBAH" ; "Tol" ; CC(C)(C)c1ccc(OCc2ccccc2)c(C(C)(C)C=O)c1]

To a stirred solution of compound 7 (20 g, 0.065 mol) in toluene (300 mL), was added drop wise DIBAH (80 mL, 1 M in toluene) at about −60 to −50° C. After stirring for 2 hours, 6 N HCl (300 mL) was added to the reaction mixture and stirring was continued for 30 minutes. The organic layer was then separated, washed with 2 N HCl followed by a NaHCO$_3$ solution, then a brine solution, dried over Na$_2$SO$_4$ and concentrated in vacuo to afford the compound 8 as an oil. The product was used in the next reaction without further purification. $^1$H NMR (CDCl$_3$; 400 MHz) δ 9.61 (s), δ 7.36 (m), δ 7.25 (m), δ 6.87 (m), δ 5.06 (m), δ 1.43 (s), δ 1.33 (s).

Procedure for the preparation of 2-(2-(benzyloxy)-5-tert-butylphenyl)-2-methylpropan-1-ol (9)

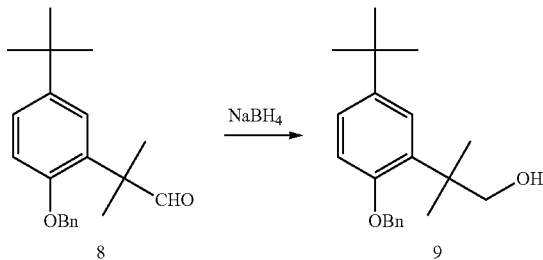 [SMILES: CC(C)(C)c1ccc(OCc2ccccc2)c(C(C)(C)C=O)c1 ; "NaBH4" ; CC(C)(C)c1ccc(OCc2ccccc2)c(C(C)(C)CO)c1]

To a stirred solution of compound 8 (9.21 g, 0.030 mol) in MeOH (150 mL) was added slowly NaBH$_4$ (2.3 g, 0.061 mol) at 0° C. After the mixture was stirred at 20° C. for 3 hours, 12 mL of 6 N HCl was added, and the mixture was stirred for an additional 30 minutes. The solution was then concentrated to about one-quarter of the original volume and extracted with EtOAc. The organic layer was separated and washed with water and brine, dried with Na$_2$SO$_4$, filtered, and then concentrated in vacuo to afford compound 9 as a white solid. NMR (DMSO-d$_6$; 400 MHz) δ 7.47 (m), δ 7.42 (m), δ 7.34 (m), δ 7.28 (m), δ 7.16 (m), δ 6.94 (m), δ 5.08 (s), δ 4.45 (t), δ 3.64 (d), δ 1.28 (s), δ 1.25 (s).

Procedure for the preparation of 2-(2-hydroxy-5-tert-butylphenyl)-2-methylpropan-1-ol (10)

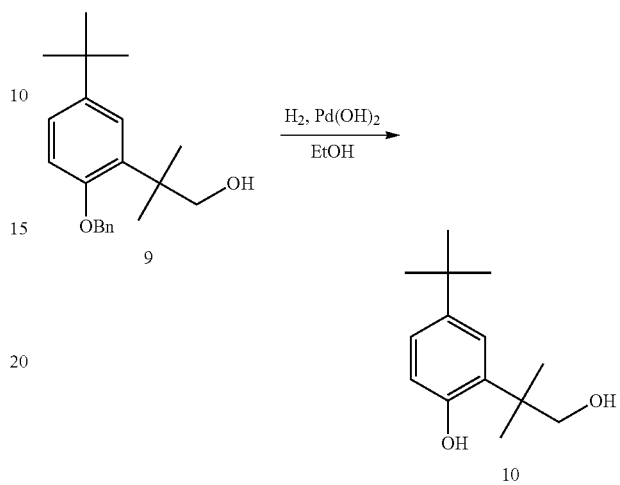

Pd(OH)$_2$ (1 g) and compound 9 (9.26 g, 0.030 mol) in MeOH (200 mL) were stirred under hydrogen at 20-30 psi pressure for 16-18 hours. The mixture was then filtered through Celite®, and the filtrate was concentrated to give compound 10 as a white solid. $^1$H NMR (DMSO-d$_6$; 400 MHz) δ 9.16 (s), δ 7.16 (d), δ 7.00 (m), δ 6.65 (m), δ 4.71 (t), δ 3.62 (d), δ 1.27 (s), δ 1.22 (s).

Procedure for the preparation of 1-((methylcaroboxy)oxy)-2-(1-((methylcaroboxy)oxy)-2-methylpropan-2-yl)-4-tert-butyl benzene (11)

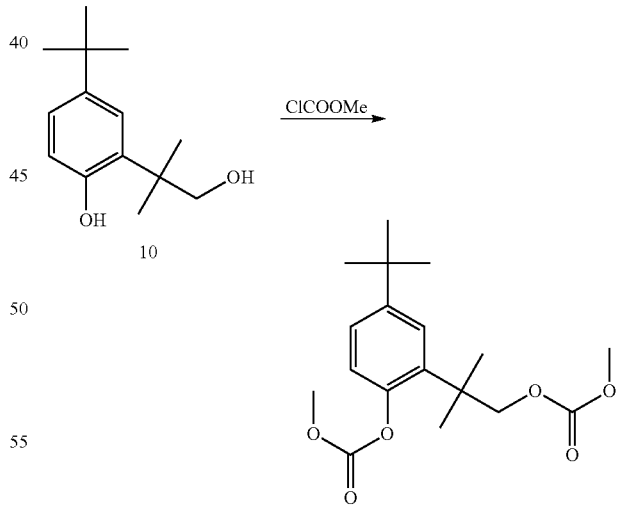

To a stirred solution of compound 10 (23.2 g, 0.10 mol), DMAP (1.44 g) and DIEA (72.8 g, 0.56 mol) in anhydrous DCM (720 mL) was added dropwise methyl chloroformate (43.5 g, 0.46 mol) in DCM (160 mL) at 0° C. After the mixture was stirred at 20° C. for 16 hours, it was washed with water, 1 N HCl and brine, dried with MgSO$_4$ and concentrated in vacuo. The residue was purified using column chromatography on silica gel (1:20 EtOAc:Petroleum ether) to give compound 11 as a white solid. $^1$H NMR (DMSO-d$_6$; 400 MHz) δ 7.32 (m), δ 7.10 (d), δ 4.26 (s), δ 3.84 (s), δ 3.64 (s), δ 1.31 (s), δ 1.28 (s).

Procedure for preparation of 1-((methylcaroboxy)oxy)-2-(1-((methylcaroboxy)oxy)-2-methylpropan-2-yl)-4-tert-butyl-5-nitro benzene (12)

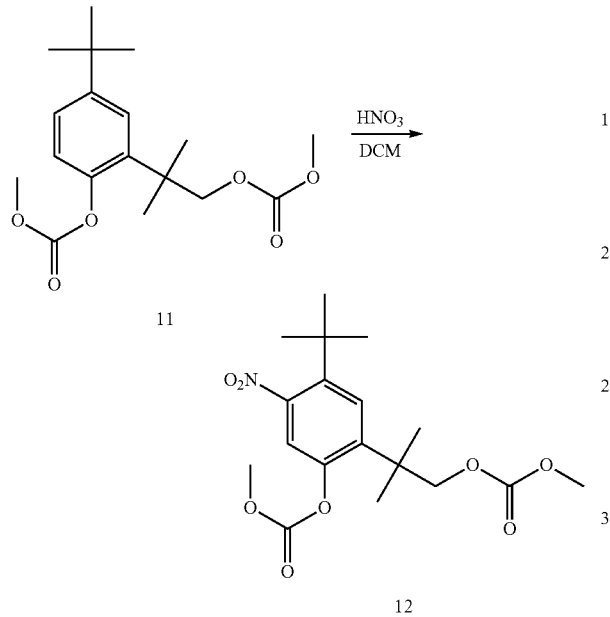

To a stirred solution of compound 11 (32 g, 0.095 mol) in DCM (550 mL) was added dropwise 98% H$_2$SO$_4$ (43 g, 0.43 mol) at 0° C. After stirring for 20 minutes at 0° C., 65% HNO$_3$ (16.2 g, 0.17 mol) was added to the mixture dropwise at 0° C. The mixture was then stirred at 1-10° C. for 4 hours and then ice-water (200 mL) was added. The aqueous layer was separated and extracted with DCM (200 mL×3) and the combined organic layers were washed with water (aq), NaHCO$_3$ and brine, then dried with MgSO$_4$ and concentrated in vacuo. The residue was purified via column chromatography on silica gel (1:20 EtOAc:Petroleum ether) to afford crude compound 12 as an oil.

Procedure for the preparation of 2-tert-butyl-5-((methylcaroboxy)oxy)-4-(1-((methylcaroboxy)oxy)-2-methylpropan-2-yl) aniline (13)

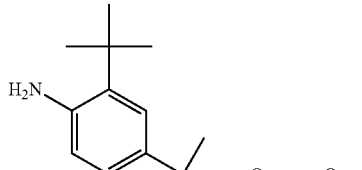

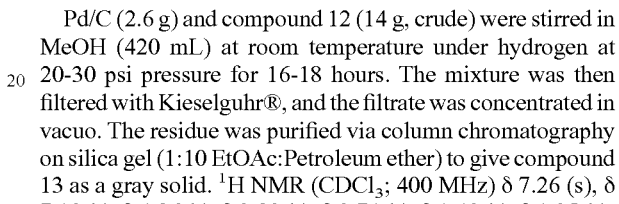

Pd/C (2.6 g) and compound 12 (14 g, crude) were stirred in MeOH (420 mL) at room temperature under hydrogen at 20-30 psi pressure for 16-18 hours. The mixture was then filtered with Kieselguhr®, and the filtrate was concentrated in vacuo. The residue was purified via column chromatography on silica gel (1:10 EtOAc:Petroleum ether) to give compound 13 as a gray solid. $^1$H NMR (CDCl$_3$; 400 MHz) δ 7.26 (s), δ 7.19 (s), δ 4.26 (s), δ 3.89 (s), δ 3.74 (s), δ 1.40 (s), δ 1.35 (s).

Procedure for the preparation of N-(2-tert-butyl-5-((methylcaroboxy)oxy)-4-(1-((methylcaroboxy)oxy)-2-methylpropan-2-yl)phenyl)-4-oxo-1,4-dihydro-quinoline-3-carboxamide (14)

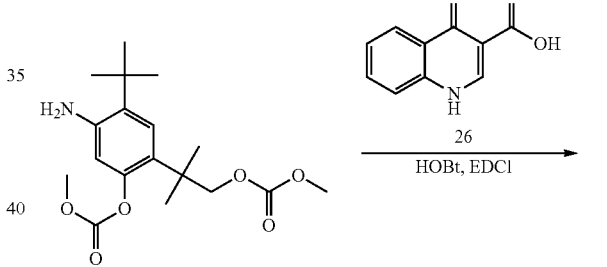

To a stirred solution of compound 26 (5.0 g, 0.026 mol) in anhydrous DMF (120 mL) was added EDCI (5.6 g, 0.029 mol), HOBT (3.8 g, 0.028 mol) and DIEA (6.6 g, 0.051 mol) at 0° C. After stirring for 1 hour, the mixture was added dropwise a solution of compound 13 (3.0 g, 0.008 mol) in DCM (30 ml) at 0° C. The mixture was stirred at 25° C. for 72 hours, and then was concentrated in vacuo. The residue was dissolved in EtOAc (225 mL) and washed with water (120 mL×1), 1N HCl (120 mL) and brine, dried with Na₂SO₄ and concentrated in vacuo. The residue was purified via column chromatography on silica gel (1:1 EtOAc:Petroleum ether) to give compound 14 as a white solid. ¹H NMR (400 MHz, CDCl₃) δ 12.34 (s, 1H), 11.58 (s, 1H), 9.07 (s, 1H), 8.42 (d, 1H), 7.66 (s, 1H), 7.51 (s, 1H), 7.47 (s, 1H), 7.39 (s, 1H), 6.72 (s, 1H), 4.34 (s, 2H), 3.82 (s, 3H), 3.74 (s, 3H), 1.41 (s, 9H), 1.40 (s, 6H).

Procedure for the preparation of N-(2-tert-butyl-5-hydroxy-4-(1-hydroxy-2-methylpropan-2-yl)phenyl)-4-oxo-1,4-dihydroquinoline-3-carboxamide (27)

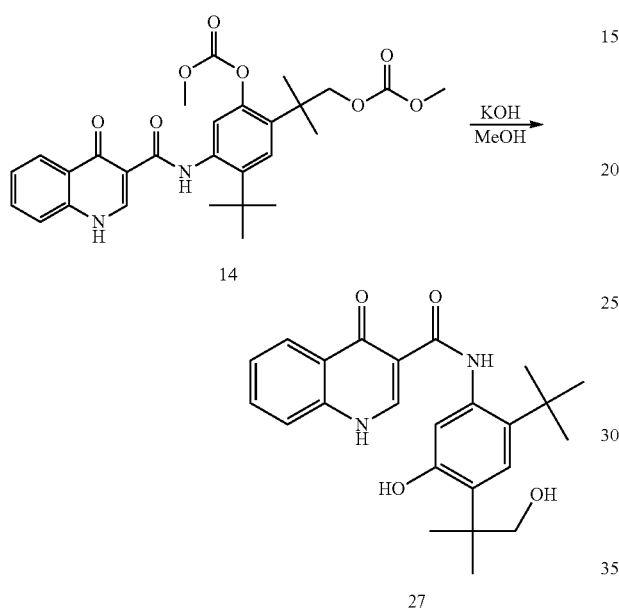

To a stirred solution of KOH (1.2 g, 0.02 mol) in MeOH (80 mL) was added compound 14 (1.9 g, 0.0036 mol) at 0° C. After stirring for 2-3 hours at 5-15° C., the mixture was concentrated to dryness. The residue was then triturated in water (10 mL), filtered, washed with DCM and dried in vacuo for 24 hours to give compound 27 as a white solid. ¹H NMR (DMSO-d₆; 400 MHz) δ 12.77 (s), δ 8.86 (s), δ 8.20 (d), δ 7.55 (d), δ 7.42 (t), δ 7.16 (q), δ 7.02 (s), δ 6.85 (m), δ 3.55 (s), δ 1.55 (s), δ 1.35 (s), δ 1.27 (s). MS Found (M+H) 409.2

Example 2

Alternative Total Synthesis of N-(2-tert-butyl-5-hydroxy-4-(1-hydroxy-2-methylpropan-2-yl)phenyl)-4-oxo-1,4-dihydroquinoline-3-carboxamide (27)

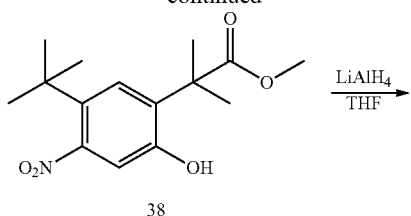

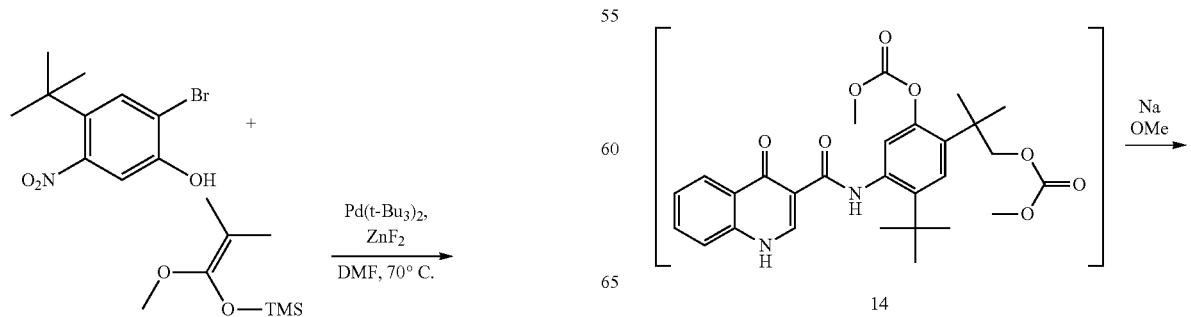

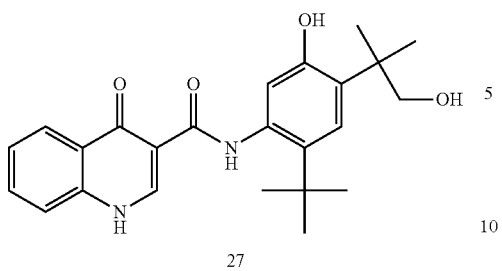

27

Procedure for the preparation of methyl 2-(5-tert-butyl-2-hydroxy-4-nitrophenyl)-2-methylpropanoate (38)

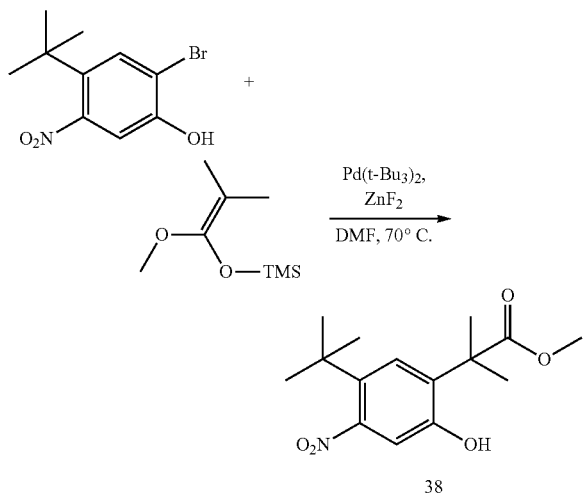

A mixture of 2-bromo-4-tert-butyl-5-nitrophenol (15.00 g, 54.72 mmol), bis(tri-tert-butylphospine)palladium(0) (1.422 g, 2.783 mmol), zinc fluoride (2.82 g, 27.27 mmol), methyl trimethylsilyl dimethylketene acetal (MTDA) (19.35 g, 111.0 mmol), and dimethylformamide (150 mL) was heated at 70° C. for 18 h. The mixture was cooled to room temperature and diluted with water. After stirring for one hour, the aqueous phase was extracted with MTBE. The organic phase was dried in vacuo to afford the crude product as a brown solid. Purification of the product was accomplished by trituration in n-heptane. $^1$H-NMR (400 MHZ, DMSO-d6) δ 10.38 (s, 1H); 7.37 (s, 1H); 6.79 (s, 1H); 3.54 (s, 3H); 1.45 (s, 6H); 1.32 (s, 9H)

Procedure for the preparation of 4-tert-butyl-2-(1-hydroxy-2-methylpropan-2-yl)-5-nitrophenol (39)

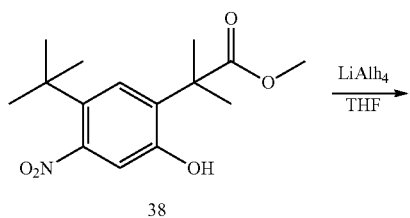

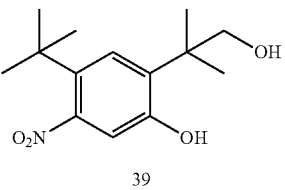

39

A 1M solution of lithium aluminum hydride in THF (11.80 mL, 11.80 mmol) was added to a solution of methyl 2-(5-tert-butyl-2-hydroxy-4-nitrophenyl)-2-methylpropanoate (5.36 g, 18.15 mmol) in THF (50 mL). The mixture was stirred at ambient temperature for 3 h, and then diluted with methanol. The mixture was acidified with 1N HCl (pH 1-2) and the aqueous phase was extracted with MTBE. The organic phase was dried in vacuo to afford 4-tert-butyl-2-(1-hydroxy-2-methylpropan-2-yl)-5-nitrophenol which was used without further purification in the next step. $^1$H-NMR (400 MHZ, DMSO-d6) δ 10.12 (s, 1H); 7.37 (s, 1H); 6.80 (s, 1H); 4.77 (s, 1H); 3.69-3.65 (m, 2H); 1.30 (s, 9H); 1.29 (s, 6H)

Procedure for the preparation of 4-tert-butyl-2-(2-methoxycarbonyloxy-1,1-dimethyl-ethyl)-5-nitro-phenyl]methyl carbonate (12)

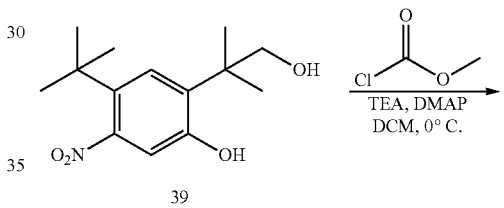

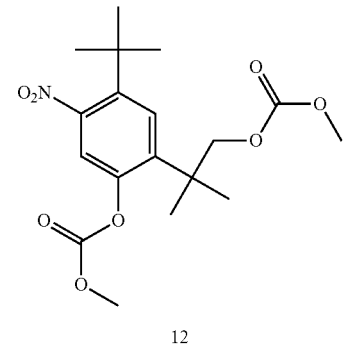

12

To a solution of 4-tert-butyl-2-(1-hydroxy-2-methylpropan-2-yl)-5-nitrophenol (1.92 g, 7.18 mmol), triethylamine (1.745 g, 17.24 mmol), and dimethylaminopyridine (87.74 mg, 0.718 mmol) in dichloromethane (30 mL) at 0° C. was slowly charged methylchloroformate (2.376 g, 25.14 mmol), keeping the temperature below 5° C. After the addition, the mixture was allowed to warm to ambient temperature and was stirred until HPLC showed complete conversion of the starting material (2-8 h). The reaction mixture was diluted with water and acidified with 1N HCl (pH 1-2). The aqueous phase was extracted with DCM and the combined organics dried in vacuo. The crude amber semi-solid was re-crystallized from methanol and dichloromethane to give the title compound as a yellow crystalline solid. $^1$H-NMR (400 MHZ, DMSO-d6) δ

7.67 (s, 1H); 7.52 (s, 1H); 4.30 (s, 2H); 3.86 (s, 3H); 3.64 (s, 3H); 1.35 (s, 9H); 1.35 (s, 6H)

Procedure for the preparation of 5-amino-4-tert-butyl-2-(2-methoxycarbonyloxy-1,1-dimethyl-ethyl)phenyl]methyl carbonate (13)

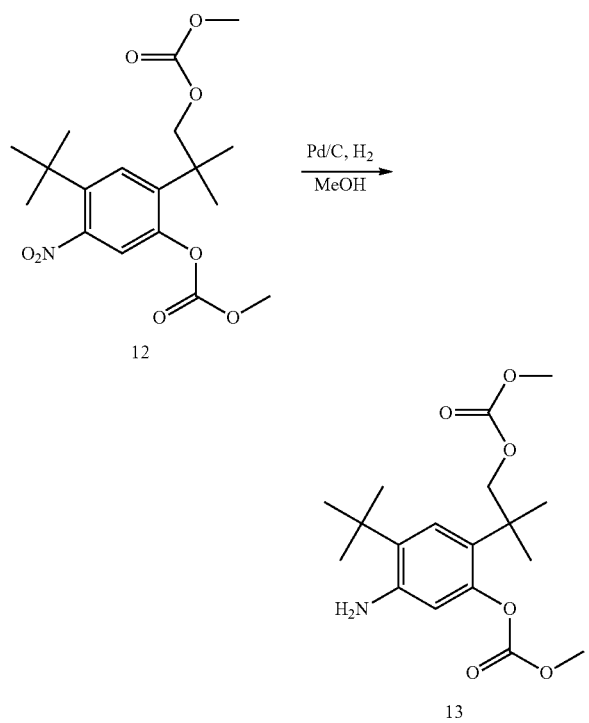

A mixture of [4-tert-butyl-2-(2-methoxycarbonyloxy-1,1-dimethyl-ethyl)-5-nitro-phenyl]methyl carbonate (1.27 g, 3.313 mmol) and Pd/C (75 mg, 0.035 mmol) in methanol (50 mL) was purged with nitrogen. After purging the flask with hydrogen, the mixture was hydrogenated for 18 hours at ambient temperature and pressure. The solution was filtered through Celite® and dried in vacuo to obtain the product as a solid. $^1$H-NMR (400 MHZ, DMSO-d6) δ 6.99 (s, 1H); 6.39 (s, 1H); 4.92 (s, 2H); 4.13 (s, 2H); 3.82 (s, 3H); 3.65 (s, 3H); 1.32 (s, 9H); 1.23 (s, 6H)

Procedure for the preparation of N-(2-tert-butyl-5-hydroxy-4-(1-hydroxy-2-methylpropan-2-yl)phenyl)-4-oxo-1,4-dihydroquinoline-3-carboxamide (27)

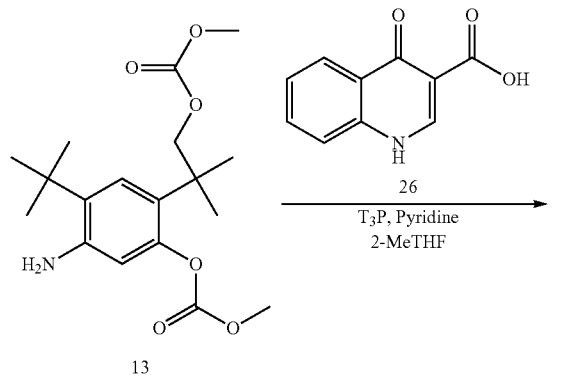

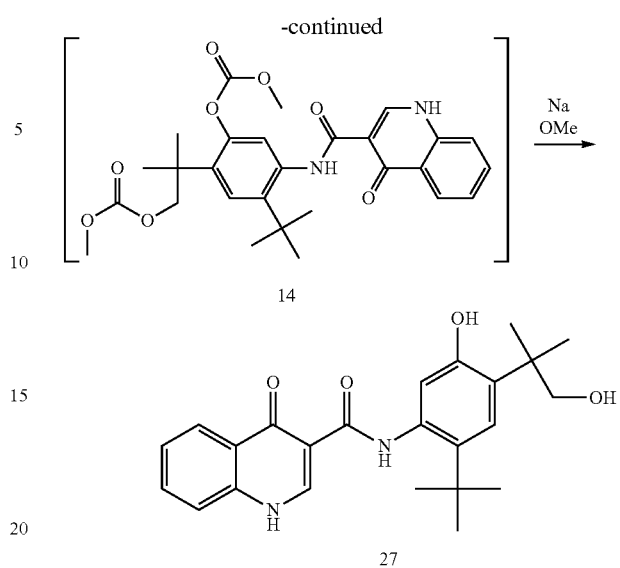

To a mixture of [5-amino-4-tert-butyl-2-(2-methoxycarbonyloxy-1,1-dimethyl-ethyl)phenyl]methyl carbonate (103 mg, 0.29 mmol), 4-oxo-1,4-dihydroquinoline-3-carboxylic acid (50 mg, 0.26 mmol), and pyridine (42 mg, 0.53 mmol) in 2-MeTHF (3.0 mL) was charged T3P as a 50 wt % solution in 2-MeTHF (286 mg, 0.45 mmol). The mixture was heated to 50° C. for 18 h. After cooling to ambient temperature, the mixture was diluted with water. The organic phase was separated and again washed with water. Sodium methoxide (39 mg, 0.72 mmol) was charged to the organic phase and the solution stirred for 2 hours. The reaction was quenched with 1N HCl, and after separating the phases, the organic phase was washed with 0.1N HCl. The organic phase was than dried in vacuo to yield Compound 27 as a solid. The $^1$H-NMR spectrum was consistent with that reported above.

Example 3

Total Synthesis of 2-(5-tert-butyl-2-hydroxy-4-(4-oxo-1,4-dihydroquinoline-3-carboxamido)phenyl)-2-methylpropanoic acid (28)

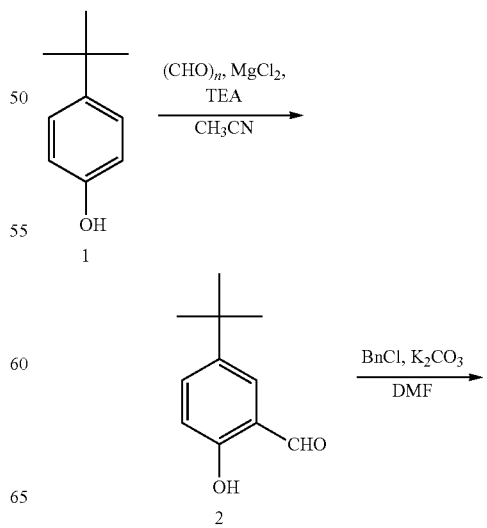

-continued
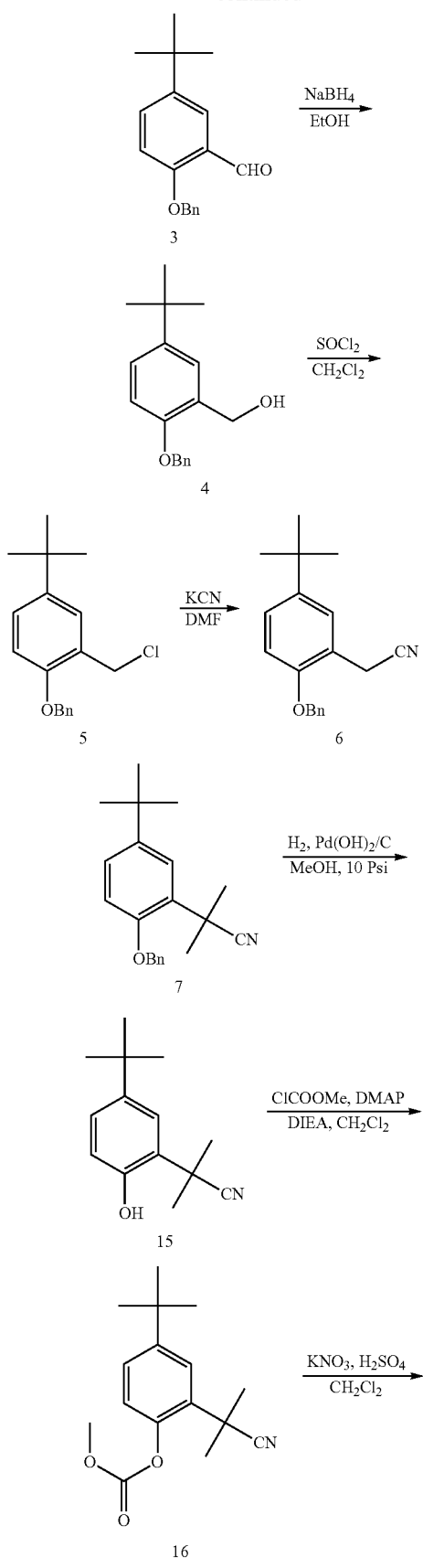
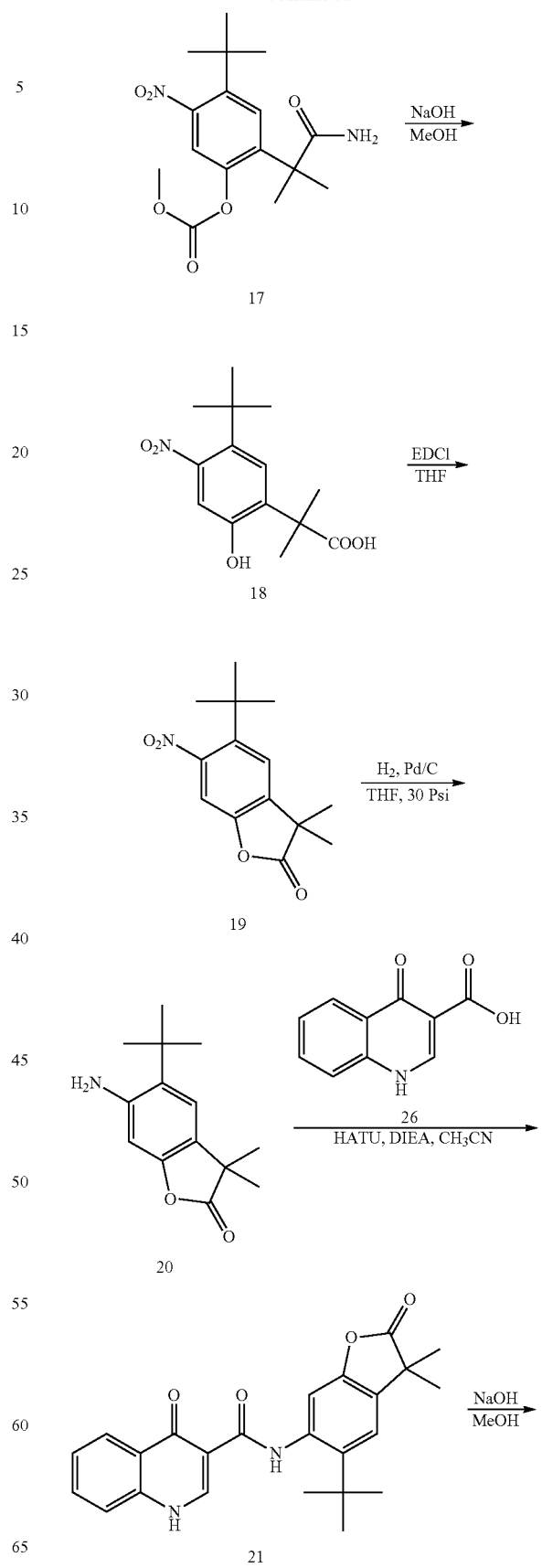

-continued

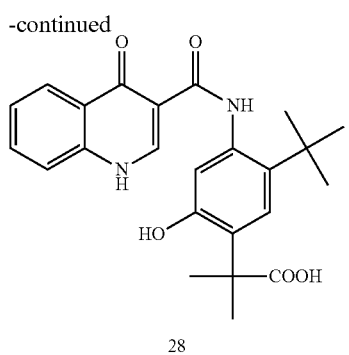

28

Procedure for the preparation of 2-(5-tert-butyl-2-hydroxyphenyl)-2-methylpropanenitrile (15)

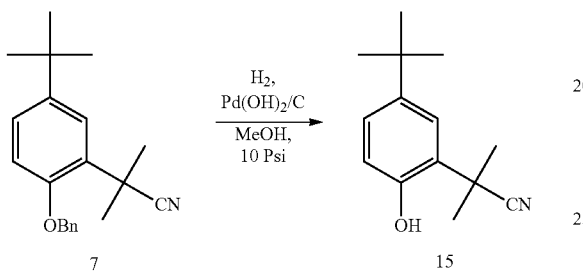

Pd(OH)$_2$/C (2.0 g) and compound 7 (20.0 g, 0.104 mol) were stirred in MeOH (150 mL) at room temperature under hydrogen at 10 psi pressure for 16-18 hours. The mixture was then filtered through a pad of Celite®, and the filtrate was concentrated to give compound 15, which was used in the next reaction without further purification. $^1$H NMR (DMSO-d$_6$; 400 MHz) δ 9.83 (s), δ 7.24 (s), δ 7.18 (m), δ 6.80 (m), δ 1.71 (s), δ 1.24 (s).

Procedure for the preparation of 4-tert-butyl-2-(2-cyanopropan-2-yl)phenyl methyl carbonate (16)

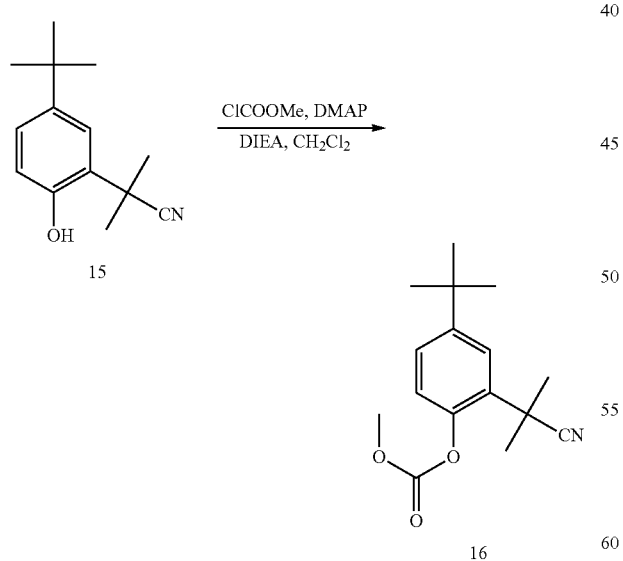

To a stirred mixture of compound 15 (126.6 g, 0.564 mol), DMAP (6.0 g) and DIEA (188 g, 1.46 mol) in anhydrous DCM (1500 mL) was added dropwise methyl chloroformate (110 g, 1.17 mol) in anhydrous DCM (300 mL) at 0° C. within 2 hours. After stirring for 12 hours at 0° C., ice-water (1.5 L) was added and the mixture was stirred at 0° C. for 30 minutes. The organic layer was separated and washed with 1 N HCl, water, and brine. The DCM solution was dried over MgSO$_4$ and concentrated in vacuo to give compound 16 as a yellow solid. $^1$H NMR (DMSO-d$_6$; 400 MHz) δ 7.47 (m), δ 7.39 (d), δ 7.24 (d), δ 3.84 (s), δ 1.71 (s), δ 1.30 (s).

Procedure for the preparation of 2-(1-amino-2-methyl-1-oxopropan-2-yl)-4-tert-butyl-5-nitrophenyl methyl carbonate (17)

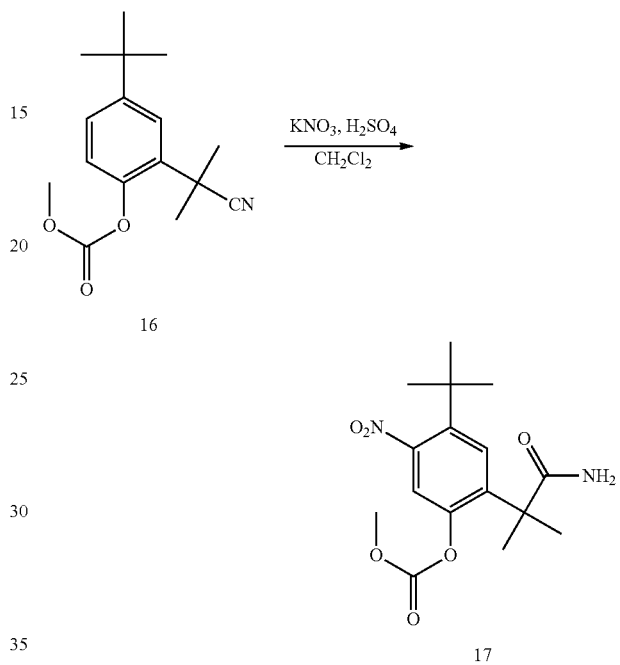

To a stirred mixture of compound 16 (10.0 g, 36.3 mmol) and KNO$_3$ (5.51 g, 54.5 mmol) in DCM (1000 mL) was added dropwise 98% H$_2$SO$_4$ (145.4 g, 1.45 mol) at 0° C. The mixture was stirred at 30° C. for 4 days. The H$_2$SO$_4$ layer was then separated and poured into ice-water (50 g) and then extracted with DCM (100 mL×3). The combined organic layers were washed with water, aqueous NaHCO$_3$ solution and brine, then dried over MgSO$_4$ and concentrated in vacuo. The residue was purified via column chromatography on silica gel (Petroleum ether/EtOAc 20:1→10:1→5:1→3:1) to give compound 17 as a yellow solid. $^1$H NMR (CDCl$_3$; 400 MHz) δ 8.05 (s), δ 7.74 (s), δ 7.61 (s), δ 7.32 (s), δ 5.32 (s), δ 3.91 (s), δ 3.92 (s), δ 1.62 (s), δ 1.59 (s), δ 1.42 (s), δ 1.38 (s).

Procedure for the preparation of 2-(5-tert-butyl-2-hydroxy-4-nitrophenyl)-2-methylpropanoic acid (18)

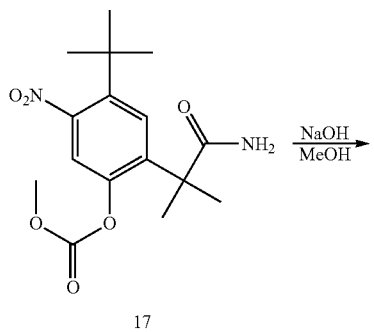

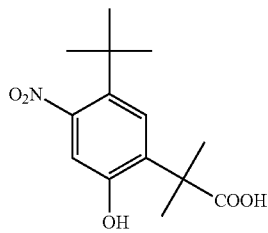

18

To a mixture of compound 17 (7.3 g, 21.6 mmol) in methanol (180 mL) was added water (18 mL) and NaOH (8.64 g, 216 mmol). The solution was heated and maintained at reflux for 3 days. The solvent was evaporated in vacuo and the residue was dissolved in 140 mL of water. Then the solution was acidified to pH 2 by the addition of 2N HCl. The aqueous phase was extracted with ethyl acetate (100 mL×3), and the combined organic phases were washed with water and brine, dried over anhydrous $Na_2SO_4$ and then concentrated to give compound 18 as a yellow solid, which was used in the next reaction without further purification.

Procedure for the preparation of 5-tert-butyl-3,3-dimethyl-6-nitrobenzofuran-2(3H)-one (19)

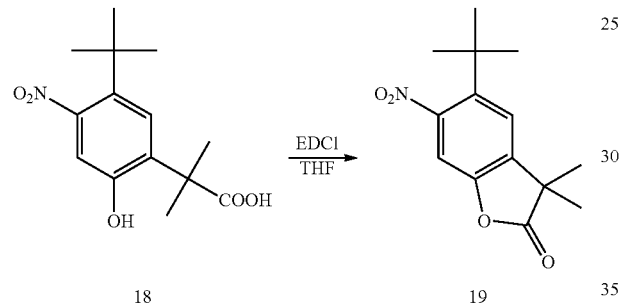

To a solution of compound 18 (7.10 g, 25.2 mmol) in 710 mL of anhydrous THF was added EDCI (14.5 g, 75.6 mmol). The resulting suspension was left stirring at 30° C. overnight. The precipitate was filtered and thoroughly washed with DCM. The filtrate was concentrated to dryness and the residue was dissolved in DCM (100 mL). The solution was washed with water (50 mL×2) and brine (50 mL×1). The DCM layer was then dried over anhydrous $Na_2SO_4$ and concentrated to give the crude product, which was purified via column chromatography on silica gel (Petroleum ether/EtOAc 200:1→100:1→50:1) to give compound 19 as a white solid. $^1$H NMR (CDCl$_3$; 400 MHz) δ 7.36 (s), δ 7.10 (s), δ 1.53 (s), δ 1.41 (s).

Procedure for the preparation of 6-amino-5-tert-butyl-3,3-dimethylbenzofuran-2(3H)-one (20)

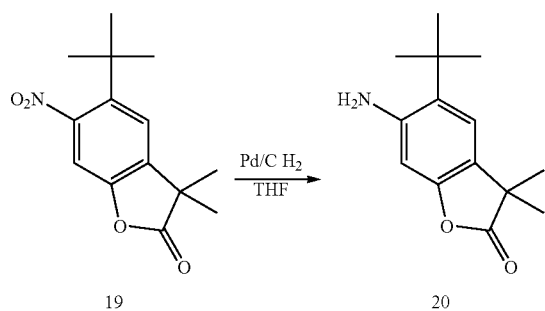 [SMILES: CC(C)(C)c1cc2c(cc1[N+](=O)[O-])OC(=O)C2(C)C ; CC(C)(C)c1cc2c(cc1N)OC(=O)C2(C)C ; "THF"]

Pd/C (1.50 g) and compound 19 (3.00 g, 1.14 mmol) were suspended in THF (1500 mL) at 25° C. under hydrogen at 30 psi for 4 hours. The mixture was then filtered through a pad of Celite®, and the filtrate was concentrated in vacuo to give compound 20 as a white solid. $^1$H NMR (DMSO-d$_6$; 400 MHz) δ 7.05 (s), δ 6.49 (s), δ 5.01 (s), δ 1.35 (s), δ 1.33 (s).

Procedure for the preparation of N-(5-tert-butyl-3,3-dimethyl-2-oxo-2,3-dihydrobenzofuran-6-yl)-4-oxo-1,4-dihydroquinoline-3-carboxamide (21)

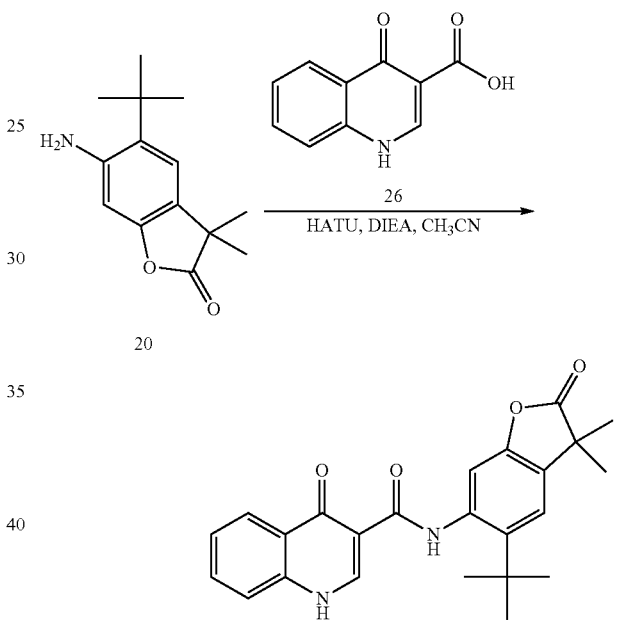

A suspension of HATU (17.6 g, 46.3 mol) and compound 26 (8.36 g, 44.2 mmol) in anhydrous acetonitrile (1 L) was stirred at room temperature for 1 hour. Compound 20 (3.40 g, 14.6 mmol) was added to the suspension, and then DIEA (11.5 g, 89.0 mmol) was added dropwise. The mixture was stirred at 45° C. for 4 days. The resulting precipitate was filtered and thoroughly washed with DCM. The filtrate was concentrated to dryness and the residue was dissolved in DCM (200 mL) and washed with 1N HCl (200 mL×2) followed by 5% aqueous NaHCO$_3$ (200 mL×3) and then brine (200 mL×1). The mixture was then dried over $Na_2SO_4$ and concentrated in vacuo. The residue was purified via column chromatography on silica gel ($CH_2Cl_2$/MeOH 100:1→50:1) to give compound 21 as a light yellow solid. $^1$H-NMR (400 MHZ, DMSO-d6) δ 12.96 (d J 6.4 Hz, 1H); 12.1 (s, 1H); 8.9

(d, J=6.4 Hz, 1H); 8.33 (d, J=8 Hz, 1H); 7.84-7.75 (m, 2H); 7.55-7.48 (m, 3H); 1.47 (s, 6H); 1.45 (s, 9H).

Procedure for the preparation of 2-(5-tert-butyl-2-hydroxy-4-(4-oxo-1,4-dihydroquinoline-3-carboxamido)phenyl)-2-methylpropanoic acid (28)

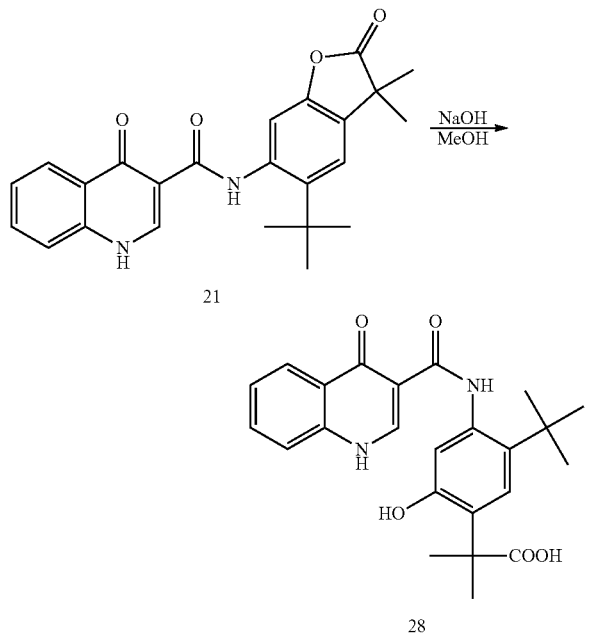

To a stirred solution of compound 21 (0.9 g, 2.45 mmol) in MeOH (50 mL) was added NaOH (1.5 g, 37.5 mmol) at 0° C. After stirring for 16 hours at 40° C., the solvent was evaporated in vacuo, then the residue was dissolved in $H_2O$ (50 ml). The precipitate was filtered and the filtrate was washed with DCM (100 mL×1) and ethyl acetate (100 mL×1). The aqueous layer was acidified with 2N HCl to pH 1-2. The precipitate was filtered and washed with $H_2O$ (80 mL) and heptane (50 mL). It was dried in vacuo to give compound 28 as a white solid. $^1$H NMR (DMSO-$d_6$; 400 MHz) δ 12.85 (s), δ 11.84 (s), δ 11.77 (s), δ 9.39 (s), δ 8.86 (s), δ 8.33 (s), δ 7.79 (m), δ 7.52 (m), δ 7.18 (s), δ 7.09 (s), δ 1.44 (s), δ 1.40 (s). MS found (M+H) 423.08

Example 4

Second alternative Synthesis of N-(2-tert-butyl-5-hydroxy-4-(1-hydroxy-2-methylpropan-2-yl)phenyl)-4-oxo-1,4-dihydroquinoline-3-carboxamide (27)

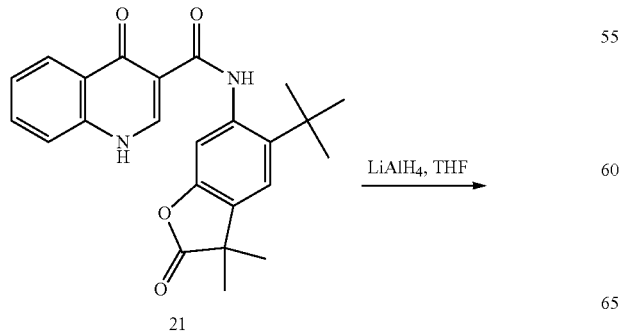

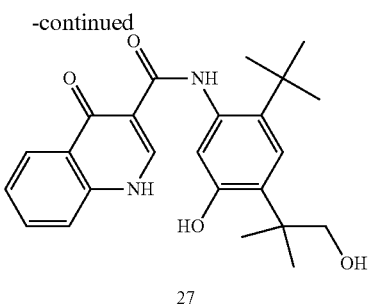

A 3-neck 50 mL round bottom flask was equipped with magnetic stirrer, nitrogen bubbler and thermocouple. Compound 21 (514 mg, 1.27 mmol) and 2-MeTHF (4 mL) are charged to the flask. The reaction mixture was stirred at room temperature. Lithium aluminum hydride (204 mg, 6.6 mmol) was added as solid until 100% conversion is achieved, which was monitored using HPLC. Potassium sodium 2,3-dihydroxybutanedioate tetrahydrate salt (50 mL of a 400 g/L solution) and MTBE (50 mL) were added to the reaction mixture. The resulting solution was stirred for 15 minutes and then let sit for 15 min. The organic layer was separated and the pH of the aqueous layer was adjusted to a pH of about 6-7 by adding tartaric acid. The aqueous layer was extracted with MTBE. The organic layer was concentrated and dried under high vacuum to provide the title compound as an off-white powder. The $^1$H-NMR spectrum was consistent with that reported above.

Example 5

Alternative Total synthesis of 2-(5-tert-butyl-2-hydroxy-4-(4-oxo-1,4-dihydroquinoline-3-carboxamido)phenyl)-2-methylpropanoic acid (28)

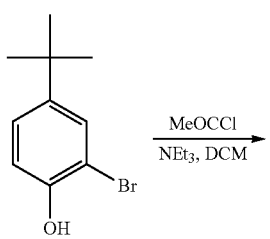

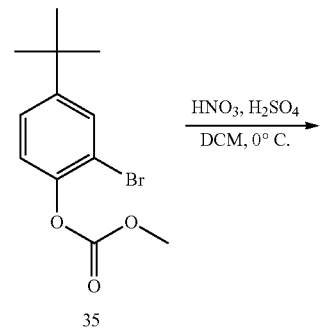

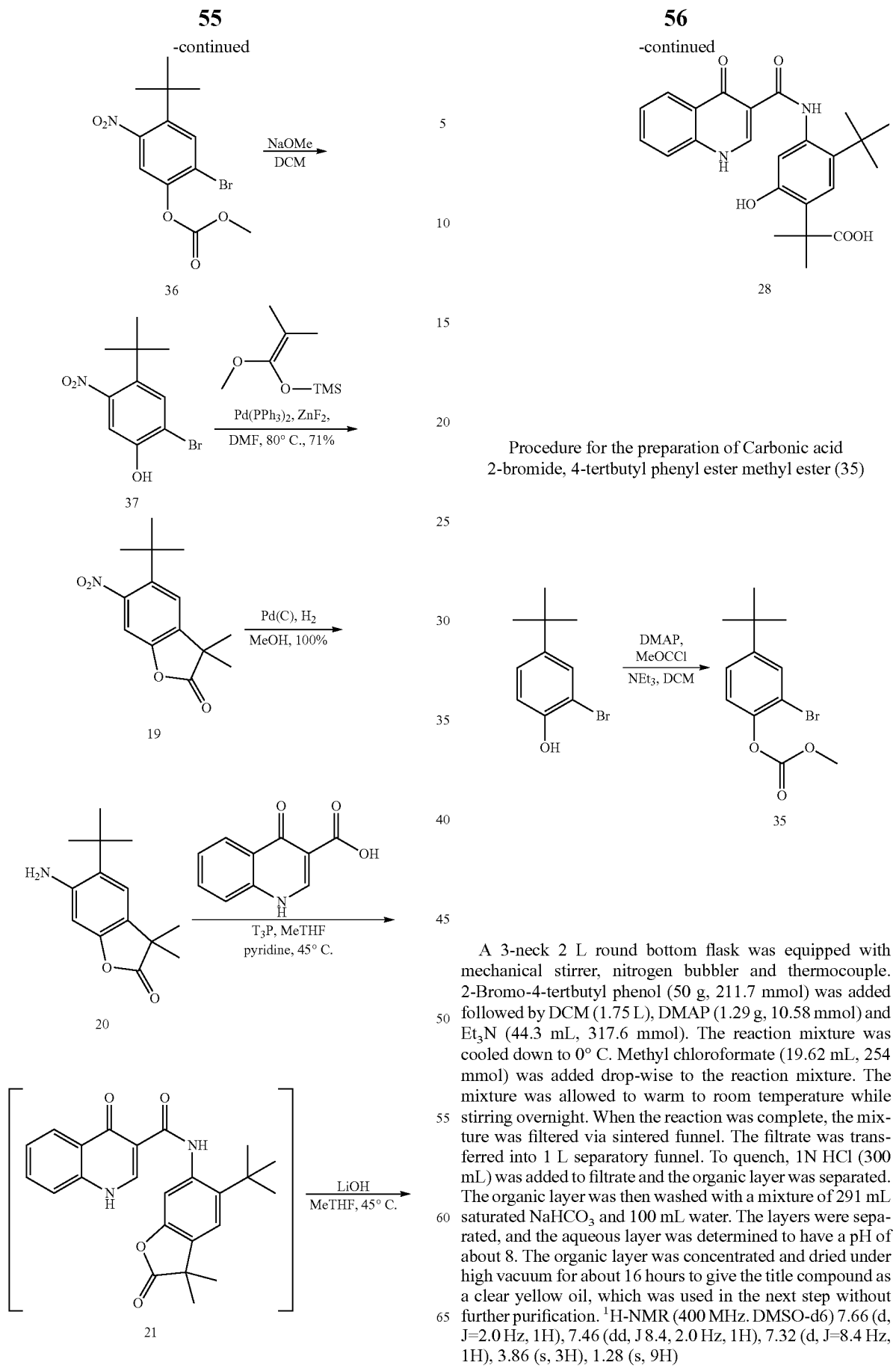

Procedure for the preparation of Carbonic acid 2-bromide, 4-tertbutyl phenyl ester methyl ester (35)

A 3-neck 2 L round bottom flask was equipped with mechanical stirrer, nitrogen bubbler and thermocouple. 2-Bromo-4-tertbutyl phenol (50 g, 211.7 mmol) was added followed by DCM (1.75 L), DMAP (1.29 g, 10.58 mmol) and $Et_3N$ (44.3 mL, 317.6 mmol). The reaction mixture was cooled down to 0° C. Methyl chloroformate (19.62 mL, 254 mmol) was added drop-wise to the reaction mixture. The mixture was allowed to warm to room temperature while stirring overnight. When the reaction was complete, the mixture was filtered via sintered funnel. The filtrate was transferred into 1 L separatory funnel. To quench, 1N HCl (300 mL) was added to filtrate and the organic layer was separated. The organic layer was then washed with a mixture of 291 mL saturated $NaHCO_3$ and 100 mL water. The layers were separated, and the aqueous layer was determined to have a pH of about 8. The organic layer was concentrated and dried under high vacuum for about 16 hours to give the title compound as a clear yellow oil, which was used in the next step without further purification. $^1$H-NMR (400 MHz. DMSO-d6) 7.66 (d, J=2.0 Hz, 1H), 7.46 (dd, J 8.4, 2.0 Hz, 1H), 7.32 (d, J=8.4 Hz, 1H), 3.86 (s, 3H), 1.28 (s, 9H)

Procedure for the preparation of (2-bromo-4-tert-butyl-5-nitro-phenyl) methyl carbonate (36)

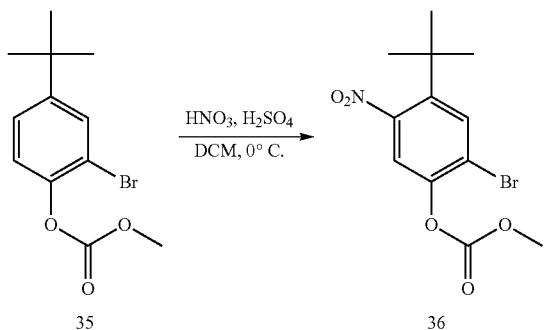 [SMILES: COC(=O)Oc1ccc(C(C)(C)C)cc1Br ; COC(=O)Oc1cc([N+](=O)[O-])c(C(C)(C)C)cc1Br]

A 3-neck 2 L round bottom flask was equipped with mechanical stirrer, nitrogen bubbler and thermocouple. Compound 35 (176 g, 612.9 mmol) and concentrated sulfuric acid (264 mL) were charged to the flask. The reaction mixture was cooled to −5° C.-0° C. Nitric acid (28.6 mL, 612.9 mmol) was added drop-wise and the reaction mixture was stirred at 0° C. for 2 hours. When complete, water (264 mL) was added followed by MTBE (264 mL). The solution was stirred for 15 minutes, then let stand for 15 minutes. The organic layer was separated, concentrated and dried under high vacuum to give the title compound as a dark brown oil, which was used in the next step without further purification. $^1$H-NMR (400 MHz. DMSO-d6) 7.96 (s, 1H), 7.92 (s, 1H), 3.89 (s, 3H), 1.34 (s, 9H)

Procedure for the preparation of 2-bromo-4-tert-butyl-5-nitro-phenol (37)

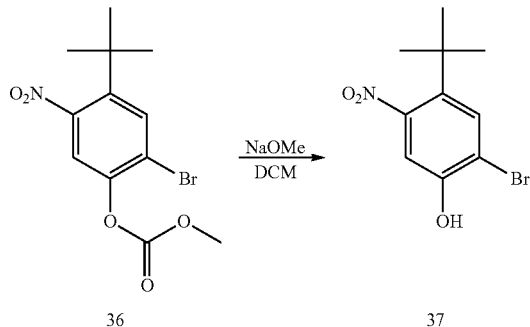 [SMILES: COC(=O)Oc1cc([N+](=O)[O-])c(C(C)(C)C)cc1Br ; CC(C)(C)c1cc(Br)c(O)cc1[N+](=O)[O-] ; "NaOMe"]

(2-Bromo-4-tert-butyl-5-nitro-phenyl)methyl carbonate (72.9 g, 219.5 mmol) was charged to a reactor and DCM (291.6 mL) was added. The yellow reaction solution was cooled using an ice bath. Sodium methoxide (67.04 g, 69.11 mL of 5.4 M, 373.2 mmol) was added portion-wise at 2.2-6.9° C. After complete addition, the reaction was slowly warmed to ambient temperature. When complete, the reaction was cooled to 0° C. and quenched with 1M HCl (373.2 mL, 373.2 mmol). The biphasic mixture was stirred for 20 min and transferred to a separatory funnel. The organic layer was separated and washed with water (300 mL) followed by brine (300 ml). The organic layer was concentrated and the crude product dried under high vacuum. The product was further purified using Supercritical Fluid Chromatography (SFC) separation on a Berger MultiGram III (Mettler Toledo AutoChem, Newark Del.). The method conditions were 20% methanol at 250 mL/min on a PPU column (30*150) from Princeton Chromatography, 100 bar, 35 C, 220 nm. An injection of 3.5 mL of a 55-70 mg/mL solution was injected. The data was collected using SFC ProNTo software. The purified product received from SFC purification was a methanol solvate. To remove the methanol, an azeotropic distillation was performed. The dark yellow solid, 2-bromo, 4-tertbuyl, 5-nitro phenol methanol solvate, (111.3 g, 59.9 mmol) was charged to a 1 L round bottom flask, followed by heptane (500 mL). The slurry is heated to 64° C. to obtain a clear solution. The solvent was distilled under reduced pressure (649 mbar) for 30 minutes and then stripped to dryness. This procedure was repeated three times until no MeOH was detected by $^1$H-NMR. The product was dried under high vacuum for 16 hours to give the product as a dark yellow semi solid. $^1$H-NMR (400 MHZ, DMSO-d6) δ 11.2 (bs, OH), 7.69 (s, 1H); 7.03 (s, 1H); 1.30 (s, 9H)

Procedure for the preparation of 5-tert-butyl-3,3-dimethyl-6-nitrobenzofuran-2(3H)-one (19)

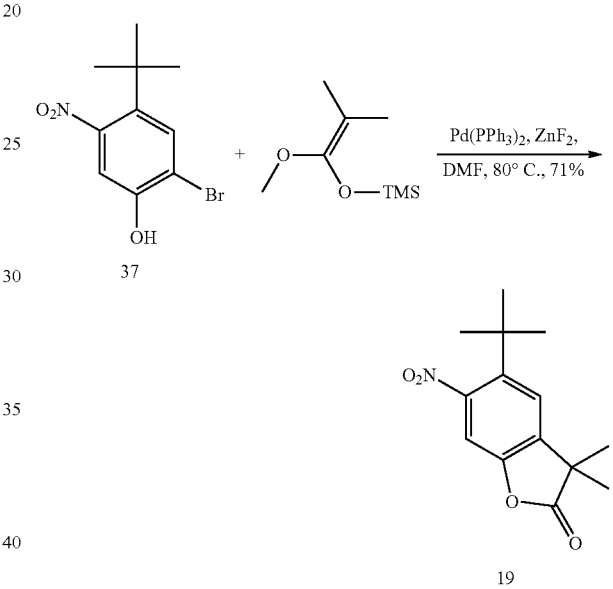

Difluorozinc (6.093 g, 58.92 mmol) was added to a round bottomed flask, which was flushed with nitrogen. Pd(tBu₃P)₂ (2 g, 3.835 mmol) was then added under nitrogen stream. 2-Bromo-4-tert-butyl-5-nitro-phenol (16.15 g, 58.92 mmol) dissolved in DMF (80.75 mL) was then added to the flask. The reaction mixture was an orange suspension. (1-Methoxy-2-methyl-prop-1-enoxy)trimethylsilane (21.61 g, 25.13 mL, 117.8 mmol) was added to the mixture and the resulting mixture was heated to 80° C. and stirred for 16 h. When complete, the reaction mixture was cooled to ambient temperature and filtered through Celite®. The filter cake was washed with MTBE (536.0 mL) and water (893.3 mL) was added to the filtrate. The mixture was stirred for 15 min and settled for another 15 min. The layers were separated and 0.5M HCl (500 mL, 250.0 mmol) was added to the organic phase. The layers were separated and the organic layer was washed with water (500 mL). The layers were separated and the organic layer was washed with NaCl (500 mL; 8 wt %). The organic layer was separated and the solvent removed in vacuo. The crude product was obtained as a brown crystalline solid and was then purified through a silica plug, using hexane:MTBE 20:1-10:1 as an eluent. The fractions containing product were combined and the solvent removed in vacuo to give the pure product as a white crystalline solid. ¹H-NMR (400 MHZ, DMSO-d6) δ 7.80 (s, 1H); 7.62 (s, 1H); 1.49 (s, 6H); 1.34 (s, 9H)

Procedure for the preparation of 6-amino-5-tert-butyl-3,3-dimethylbenzofuran-2(3H)-one (20)

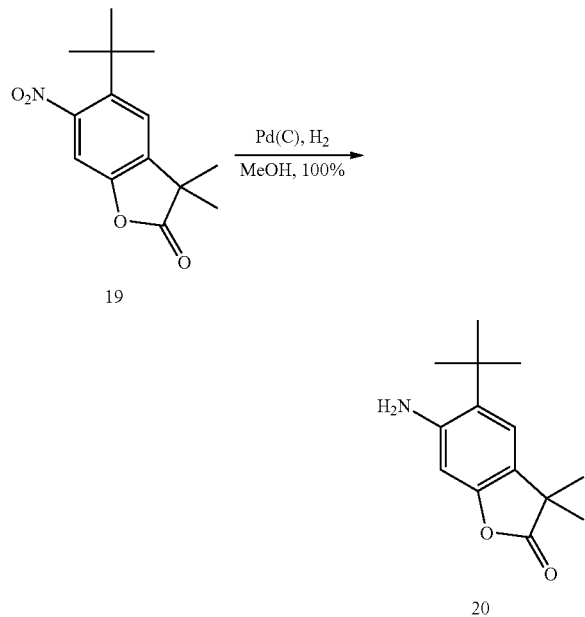

Palladium on carbon (wet; 5 wt %) was placed into a round bottomed flask under nitrogen flow. 5-Tert-butyl-3,3-dimethyl-6-nitro-benzofuran-2-one (4.7 g, 17.85 mmol) was then added to the vessel. Methanol (120 mL) was then carefully charged to the vessel under nitrogen atmosphere. The vessel was then purged with N₂, evacuated, then charged with hydrogen gas. The vessel was evacuated and re-charged with hydrogen gas, and then a continuous hydrogen gas stream was introduced. After completion, the reaction was filtered through Celite® and the cake was washed with MeOH (300 ml). The solvent was removed in vacuo and the product dried under high vacuum to give a white crystalline solid. ¹H-NMR (400 MHZ, DMSO-d6) δ 7.05 (s, 1H); 6.48 (s, 1H); 5.02 (s, 2H, NH₂); 1.34 (s, 6H); 1.30 (s, 9H)

Procedure for the preparation of N-(5-tert-butyl-3,3-dimethyl-2-oxo-2,3-dihydrobenzofuran-6-yl)-4-oxo-1,4-dihydroquinoline-3-carboxamide (21)

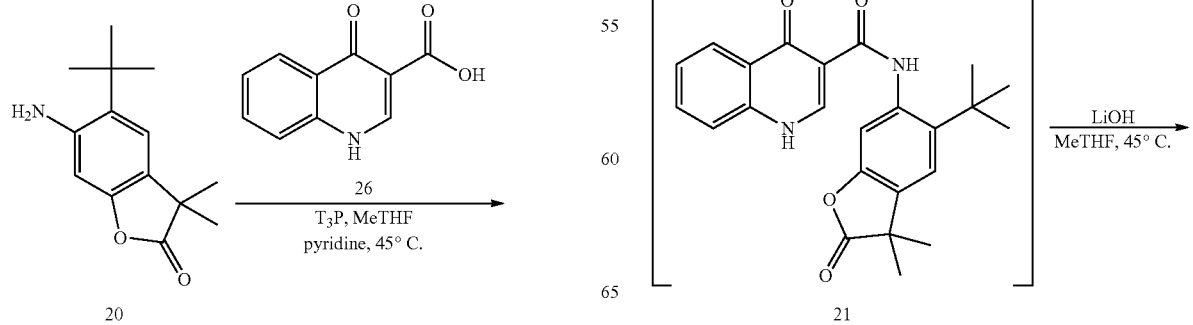

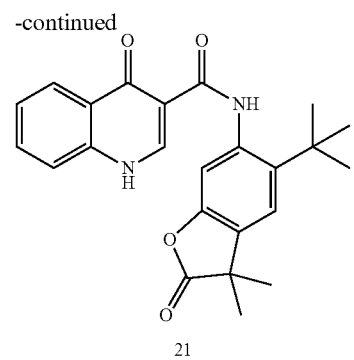

A reaction vessel was charged with compound 26 (2.926 g, 15.43 mmol), Compound 20 (4.32 g, 18.52 mmol), 2-MeTHF (35.99 mL), and subsequently 50% T3P in 2-MeTHF (13.36 g, 21.00 mmol). Pyridine (2.441 g, 2.496 mL, 30.86 mmol) was added and the suspension heated at 47.5° C.±5° C. for 18 h. After completion, the reaction was cooled to ambient temperature and 2-MeTHF (36) and water (30 ml) were added. The layers were split and the organic layer was washed with 10 wt % citric acid solution (30 ml), water (30 ml) and twice with NaHCO₃ (20 ml). The organic layer was washed with brine (50 ml), separated and the solvent removed in vacuo. The crude product was dissolved in MTBE (100 ml) and hexane (200 ml) was added as an anti-solvent. A solid precipitated and the resulting slurry was stirred for two hours. The solid was collected by suction filtration and the cake was washed with hexane. The resulting product was dried in a vacuum oven at 55° C. with nitrogen bleed to give the title compound as a beige solid. ¹H-NMR (400 MHZ, DMSO-d6) δ 12.96 (d J 6.4 Hz, 1H); 12.1 (s, 1H); 8.9 (d, J 6.4 Hz, 1H); 8.33 (d, J=8 Hz, 1H); 7.84-7.75 (m, 2H); 7.55-7.48 (m, 3H); 1.47 (s, 6H); 1.45 (s, 9H).

Procedure for the preparation of 2-(5-tert-butyl-2-hydroxy-4-(4-oxo-1,4-dihydroquinoline-3-carboxamido)phenyl)-2-methylpropanoic acid (28)

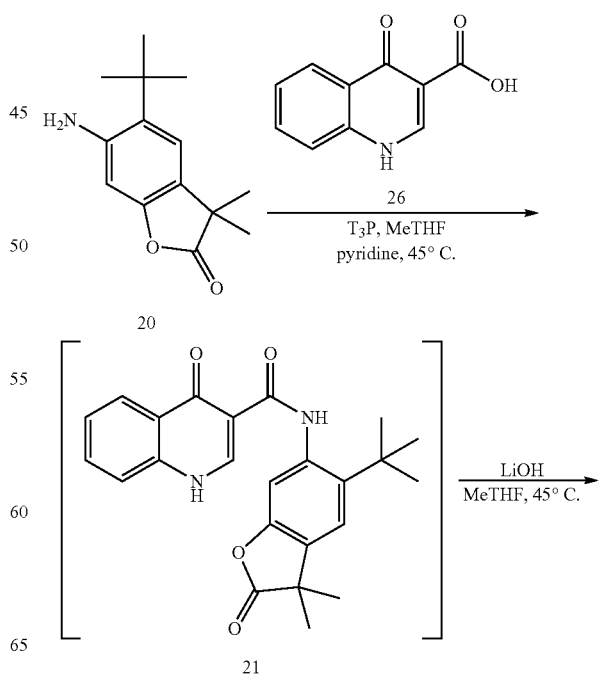

-continued

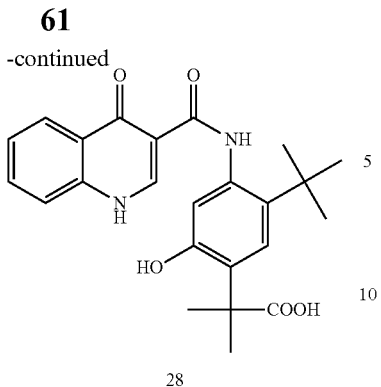

28

Compound 26 (81.30 mg, 0.4288 mmol) and Compound 20 (110 mg, 0.4715 mmol) were charged to a round bottomed flask. 2-MeTHF (1 mL) followed by 50% T3P in 2-MeTHF (371.4 mg, 0.5836 mmol) and pyridine (67.84 mg, 69.37 µL, 0.8576 mmol) in 2-MeTHF were then added. The suspension was heated at 47.5° C.±5° C. overnight. After completion, the reaction was cooled to ambient temperature. 2-MeTHF (1.014 mL) and water (811.2 µL) were added. The layers were separated and the organic layer was washed with water (811.2 µL) and twice with NaHCO$_3$ (2 mL). The organic layer was transferred into a round bottomed flask. LiOH (38.6 mg, 0.9 mmol) dissolved in water (2 mL) was added and the reaction was heated to 45° C. After completion, the layers were separated and the organic layer was discarded. The aqueous layer was cooled with an ice bath and hydrochloric acid (10.72 mL of 1.0 M, 10.72 mmol) was added to the solution until the pH reached a pH of about 3-4. The aqueous layer was extracted twice with 2-MeTHF (5 ml), and the organic layers were combined and washed with brine (5 ml). The organic layer was separated and the solvent removed in vacuo. The resulting solid was dried in a vacuum oven with nitrogen bleed at 50° C. to give the title compound. $^1$H-NMR (400 MHZ, DMSO-d6) δ 12.89 (d, J=6.8 Hz, 1H); 11.84 (s, 1H); 11.74 (s, 1H); 9.36 (s, 1H); 8.87-8.61 (d, J=6.4 Hz, 1H); 8.34-8.32 (d, J=9.1 Hz 1H); 7.83-7.745 (m, 2H); 7.17-7.09 (m, 1H); 7.17 (s, 1H); 7.09 (s, 1H); 1.43 (s, 6H); 1.40 (s, 9H)

Example 6

Procedure for the biosynthesis of N-(2-tert-butyl-5-hydroxy-4-(1-hydroxy-2-methylpropan-2-yl)phenyl)-4-oxo-1,4-dihydroquinoline-3-carboxamide (27) and 2-(5-tert-butyl-2-hydroxy-4-(4-oxo-1,4-dihydroquinoline-3-carboxamido)phenyl)-2-methylpropanoic acid (28)

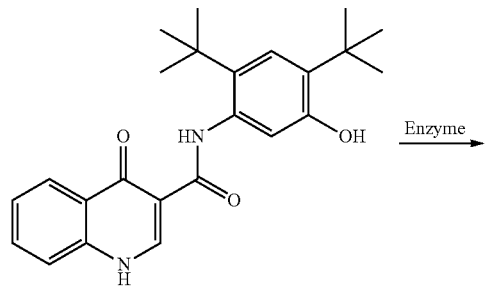

34

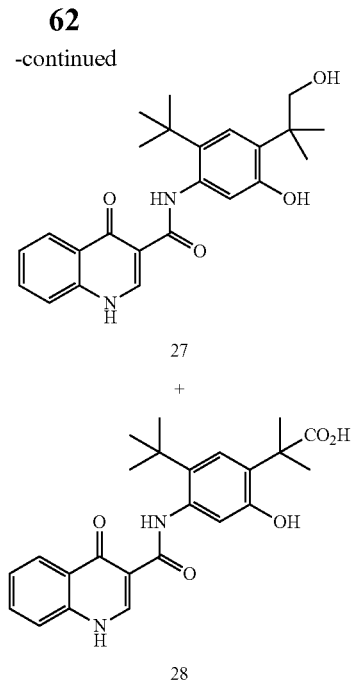

27

+

28

*Streptomyces rimosus* (DSM 40260) was purchased from DSMZ as frozen culture. This culture was used to inoculate agar slants, which were maintained and stored at 4° C. Yeast extract-malt extract-peptone (YMP) media containing yeast extract (4 g/L), malt extract (10 g/L) and soya flour (5 g/L) was prepared and sterilized at 130° C. for 60 minutes. Five flasks containing 1 L of YMP media were directly inoculated with *S. rimosus* from the agar slants. The culture was allowed to grow for 2-3 days at 30° C. with gentle agitation of approximately 100 rpm. Under these conditions, two growth types have been observed, either a cloudy solution or spherical particulates which aggregate at the bottom of the flask. The latter growth type has been shown to result in higher conversions to Compound 27. The cells were then spun down, harvested and resuspended in two flasks containing 1 L of 0.1 M potassium phosphate buffer, pH 7.0. 5.0 g of Compound 34 in 50 mL N,N-dimethylformamide (DMF) were added to the flasks. The reactions proceeded for 24 hours at 30° C. with gentle agitation of about 100 rpm at which point conversions of 7.59% Compound 27 and 1.17% Compound 28 were indicated by HPLC.

Both flasks were combined, centrifuged at 3500 rpm for 10 minutes, and re-suspended in 500 mL of methanol. This suspension was stirred vigorously for 30 minutes and then spun down again at 6000 rpm for 10 minutes. The organic layer was collected and the process was repeated two times. The methanol extracts were concentrated in vacuo to yield 2.50 g, 1.57 g and 1.11 g of solid material, respectively. The solids from these extracts were shown to contain 74.78-91.96% Compound 34, 7.66-19.73% Compound 27 and 0.39-5.49% Compound 28. In an effort to cull off a portion of Compound 34 from the bio-oxidation products, the solids from the first two extractions were combined, suspended in 250 mL methanol, agitated vigorously for 1 hour and vacuum filtered. While Compounds 27 and 28 were enriched in the filtrate (22.09 and 6.14%, respectively), the solids still also contained Compound 27 (8.96%) and Compound 28 (0.50%).

The methanol filtrate containing approximately 2.2 g of dissolved solids was adsorbed onto 4.5 g of silica and purified by flash chromatography using a gradient of 100% dichloromethane to 88:12 dichloromethane/methanol. Fractions containing Compound 27 were concentrated in vacuo and further dried via freeze-drying to obtain 130 mg of Compound 27 (98.5% purity by HPLC). A fraction containing impure Compound 28 was also concentrated in vacuo to yield less than 10 mg of solid.

The cell pellet was re-suspended in 500 mL methanol and homogenized in a BeadBeater to break apart the cells and recover any remaining product. The organic layer was obtained by centrifuging the homogenized suspension at 6000 rpm for 10 minutes. This was added to the solid obtained from the third extraction and the filtered solids from the slurry enrichment of the first two extractions and slurried at reflux overnight. The slurry was then cooled and suction filtered to obtain 1.99 g of solid. The solid was re-dissolved in 300 mL methanol which was then adsorbed onto approximately 5 g of silica and purified by flash chromatography using a gradient of 100% dichloromethane to 94:6 dichloromethane/methanol to provide 820 mg of solid containing Compound 34 and Compound 27 as well as other impurities. This was re-columned using a more gradual solvent gradient (100% DCM up to a mixture of 6% MeOH/94% DCM) to obtain an additional 89 mg of Compound 27. The $^1$H-NMR spectrum was consistent with that reported above.

Example 7

General Procedure to Test Solubility at pH 7.4

A high throughput shake flask assay was used to determine solubility of compounds in pH 7.4 buffer. To calculate the concentration of compounds in solution, two conditions per compound were run: 300 uM in 100% DMSO and 200 uM in pH 7.4 phosphate buffer with 2% DMSO present. Each sample was left to shake overnight then injected onto HPLC-UV to determine peak area using the following conditions: Phenomenex 00A-4251-B0-30×2.00 mm Luna 3u C18(2) 100A column; 0.8 mL/min flow rate; 20 uL injection volume; HPLC grade water with 0.1% formic acid and HPLC grade acetonitrile with 0.1% formic acid mobile phases; peak area determined at 254 nm. Solubility in uM was calculated using the following equation: conc.=(peak area pH 7.4)/(peak area 300 uM DMSO standard condition)*300 uM concentration of standard condition. Peaks of interest were identified in buffer conditions based on retention time (RT) of the largest area peak in the 300 uM DMSO standard condition.

Activity Assays

Example 8

General Procedure for Activity Assays

Assays for Detecting and Measuring ΔF508-CFTR Potentiation Properties of Compounds Membrane Potential Optical Methods for Assaying ΔF508-CFTR Modulation Properties of Compounds The assay utilizes fluorescent voltage sensing dyes to measure changes in membrane potential using a fluorescent plate reader (e.g., FLIPR III, Molecular Devices, Inc.) as a readout for increase in functional ΔF508-CFTR in NIH 3T3 cells. The driving force for the response is the creation of a chloride ion gradient in conjunction with channel activation by a single liquid addition step after the cells have previously been treated with compounds and subsequently loaded with a voltage sensing dye.

Identification of Potentiator Compounds

To identify potentiators of ΔF508-CFTR, a double-addition HTS assay format was developed. This HTS assay utilizes fluorescent voltage sensing dyes to measure changes in membrane potential on the FLIPR III as a measurement for increase in gating (conductance) of ΔF508 CFTR in temperature-corrected ΔF508 CFTR NIH 3T3 cells. The driving force for the response is a Cl$^-$ ion gradient in conjunction with channel activation with forskolin in a single liquid addition step using a fluorescent plate reader such as FLIPR III after the cells have previously been treated with potentiator compounds (or DMSO vehicle control) and subsequently loaded with a redistribution dye.

Solutions

Bath Solution #1: (in mM) NaCl 160, KCl 4.5, CaCl$_2$ 2, MgCl$_2$ 1, HEPES 10, pH 7.4 with NaOH.

Chloride-free bath solution: Chloride salts in Bath Solution #1 are substituted with gluconate salts.

Cell Culture

NIH3T3 mouse fibroblasts stably expressing ΔF508-CFTR are used for optical measurements of membrane potential. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm$^2$ culture flasks. For all optical assays, the cells were seeded at ~20,000/well in 384-well matrigel-coated plates and cultured for 2 hrs at 37° C. before culturing at 27° C. for 24 hours. for the potentiator assay. For the correction assays, the cells are cultured at 27° C. or 37° C. with and without compounds for 16-24 hours. Electrophysiological Assays for assaying ΔF508-CFTR modulation properties of compounds.

1. Ussing Chamber Assay

Ussing chamber experiments were performed on polarized airway epithelial cells expressing ΔF508-CFTR to further characterize the ΔF508-CFTR modulators identified in the optical assays. Non-CF and CF airway epithelia were isolated from bronchial tissue, cultured as previously described (Galietta, L. J. V., Lantero, S., Gazzolo, A., Sacco, O., Romano, L., Rossi, G. A., & Zegarra-Moran, O. (1998) *In Vitro Cell. Dev. Biol.* 34, 478-481), and plated onto Costar® Snapwell™ filters that were pre-coated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF HBE were isolated from non-smokers that did not have any known lung disease. CF-HBE were isolated from patients homozygous for ΔF508-CFTR.

HBE grown on Costar® Snapwell™ cell culture inserts were mounted in an Ussing chamber (Physiologic Instruments, Inc., San Diego, Calif.), and the transepithelial resistance and short-circuit current in the presence of a basolateral to apical Cl$^-$ gradient ($I_{SC}$) were measured using a voltage-clamp system (Department of Bioengineering, University of Iowa, Iowa). Briefly, HBE were examined under voltage-clamp recording conditions ($V_{hold}$=0 mV) at 37° C. The basolateral solution contained (in mM) 145 NaCl, 0.83 K$_2$HPO$_4$, 3.3 KH$_2$PO$_4$, 1.2 MgCl$_2$, 1.2 CaCl$_2$, 10 Glucose, 10 HEPES (pH adjusted to 7.35 with NaOH) and the apical solution contained (in mM) 145 NaGluconate, 1.2 MgCl$_2$, 1.2 CaCl$_2$, 10 glucose, 10 HEPES (pH adjusted to 7.35 with NaOH).

Identification of Potentiator Compounds

Typical protocol utilized a basolateral to apical membrane Cl$^-$ concentration gradient. To set up this gradient, normal ringers was used on the basolateral membrane, whereas apical NaCl was replaced by equimolar sodium gluconate (titrated to pH 7.4 with NaOH) to give a large Cl$^-$ concentration gradient across the epithelium. Forskolin (10 μM) and all test compounds were added to the apical side of the cell culture inserts. The efficacy of the putative ΔF508-CFTR potentiators was compared to that of the known potentiator, genistein.

2. Patch-Clamp Recordings

Total Cl⁻ current in ΔF508-NIH3T3 cells was monitored using the perforated-patch recording configuration as previously described (Rae, J., Cooper, K., Gates, P., & Watsky, M. (1991) *J. Neurosci. Methods* 37, 15-26). Voltage-clamp recordings were performed at 22° C. using an Axopatch 200B patch-clamp amplifier (Axon Instruments Inc., Foster City, Calif.). The pipette solution contained (in mM) 150 N-methyl-D-glucamine (NMDG)-Cl, 2 MgCl$_2$, 2 CaCl$_2$, 10 EGTA, 10 HEPES, and 240 µg/ml amphotericin-B (pH adjusted to 7.35 with HCl). The extracellular medium contained (in mM) 150 NMDG-Cl, 2 MgCl$_2$, 2 CaCl$_2$, 10 HEPES (pH adjusted to 7.35 with HCl). Pulse generation, data acquisition, and analysis were performed using a PC equipped with a Digidata 1320 A/D interface in conjunction with Clampex 8 (Axon Instruments Inc.). To activate ΔF508-CFTR, 10 µM forskolin and 20 µM genistein were added to the bath and the current-voltage relation was monitored every 30 sec.

Identification of Potentiator Compounds

The ability of ΔF508-CFTR potentiators to increase the macroscopic ΔF508-CFTR Cl⁻ current ($I_{\Delta F508}$) in NIH3T3 cells stably expressing ΔF508-CFTR was also investigated using perforated-patch-recording techniques. The potentiators identified from the optical assays evoked a dose-dependent increase in $I\Delta_{F508}$ with similar potency and efficacy observed in the optical assays. In all cells examined, the reversal potential before and during potentiator application was around −30 mV, which is the calculated $E_{Cl}$ (−28 mV).

Cell Culture

NIH3T3 mouse fibroblasts stably expressing ΔF508-CFTR are used for whole-cell recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For whole-cell recordings, 2,500-5,000 cells were seeded on poly-L-lysine-coated glass coverslips and cultured for 24-48 hrs at 27° C. before use to test the activity of potentiators; and incubated with or without the correction compound at 37° C. for measuring the activity of correctors.

3. Single-Channel Recordings

Gating activity of wt-CFTR and temperature-corrected ΔF508-CFTR expressed in NIH3T3 cells was observed using excised inside-out membrane patch recordings as previously described (Dalemans, W., Barbry, P., Champigny, G., Jallat, S., Dott, K., Dreyer, D., Crystal, R. G., Pavirani, A., Lecocq, J-P., Lazdunski, M. (1991) Nature 354, 526-528) using an Axopatch 200B patch-clamp amplifier (Axon Instruments Inc.). The pipette contained (in mM): 150 NMDG, 150 aspartic acid, 5 CaCl$_2$, 2 MgCl$_2$, and 10 HEPES (pH adjusted to 7.35 with Tris base). The bath contained (in mM): 150 NMDG-Cl, 2 MgCl$_2$, 5 EGTA, 10 TES, and 14 Tris base (pH adjusted to 7.35 with HCl). After excision, both wt- and ΔF508-CFTR were activated by adding 1 mM Mg-ATP, 75 nM of the catalytic subunit of cAMP-dependent protein kinase (PKA; Promega Corp. Madison, Wis.), and 10 mM NaF to inhibit protein phosphatases, which prevented current rundown. The pipette potential was maintained at 80 mV. Channel activity was analyzed from membrane patches containing ≤2 active channels. The maximum number of simultaneous openings determined the number of active channels during the course of an experiment. To determine the single-channel current amplitude, the data recorded from 120 sec of ΔF508-CFTR activity was filtered "off-line" at 100 Hz and then used to construct all-point amplitude histograms that were fitted with multigaussian functions using Bio-Patch Analysis software (Bio-Logic Comp. France). The total microscopic current and open probability ($P_o$) were determined from 120 sec of channel activity. The $P_o$ was determined using the Bio-Patch software or from the relationship $P_o=I/i(N)$, where I=mean current, i=single-channel current amplitude, and N=number of active channels in patch.

Cell Culture

NIH3T3 mouse fibroblasts stably expressing ΔF508-CFTR are used for excised-membrane patch-clamp recordings. The cells are maintained at 37° C. in 5% CO$_2$ and 90% humidity in Dulbecco's modified Eagle's medium supplemented with 2 mM glutamine, 10% fetal bovine serum, 1×NEAA, β-ME, 1× pen/strep, and 25 mM HEPES in 175 cm² culture flasks. For single channel recordings, 2,500-5,000 cells were seeded on poly-L-lysine-coated glass coverslips and cultured for 24-48 hrs at 27° C. before use.

Compounds 27 and 28 were tested for solubility using the procedure given in Example 3 and for activity using the procedure given in the assays of Example 4. The results are shown in Table 1. The compound activity is illustrated with "+++" if EC$_{50}$ (or IC$_{50}$) was measured to be less than 2.0 µM, "++" if activity was measured to be from 2 µM to 5.0 µM, "+" if activity was measured to be greater than 5.0 µM, and "−" if no data was available. The efficacy is illustrated with "+++" if efficacy was calculated to be greater than 100%, "++" if efficacy was calculated to be from 100% to 25%, "+" if efficacy was calculated to be less than 25%, and "−" if no data was available.

TABLE 1

Examples of activities and efficacies of the compounds of Formula I

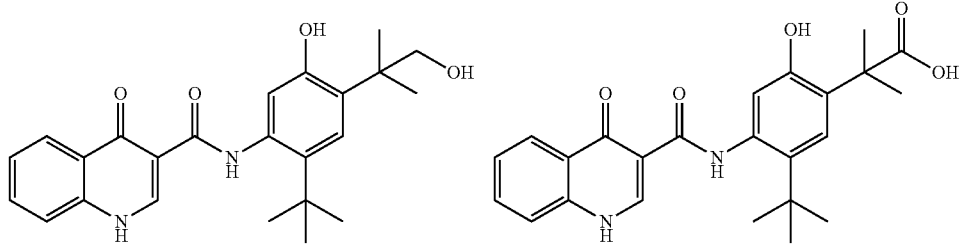

| Structure | Compound 27 | Compound 28 |
|---|---|---|
| HTSF Solubility @ pH = 7.4 | 87 uM | >200 uM |
| Optical EC$_{50}$ | +++ | ++ |
| Δ508-HBE EC$_{50}$ | +++ | +++ |

TABLE 1-continued

Examples of activities and efficacies of the compounds of Formula I

| Structure | Compound 27 | Compound 28 |
|---|---|---|
| Δ508/G551D-HBE EC$_{50}$ | +++ | ++ |
| HLM/RLM (% remain. @ 30 min) min) | ++ | +++ |
| CaV 1.2 IC$_{50}$ | + | − |

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A method of treating or lessening the severity of a disease in a patient, wherein said disease is selected from cystic fibrosis, smoke induced COPD, pancreatitis, pancreatic insufficiency, hereditary emphysema, COPD, or dry-eye disease, said method comprising administering to said patient an effective amount of a compound of Formula I:

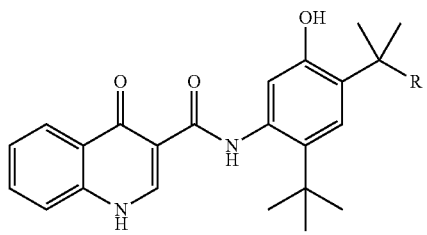

I or a pharmaceutically acceptable salt thereof, wherein R is COOH or CH$_2$OH.

2. The method of claim 1, wherein the compound of Formula I has the structure:

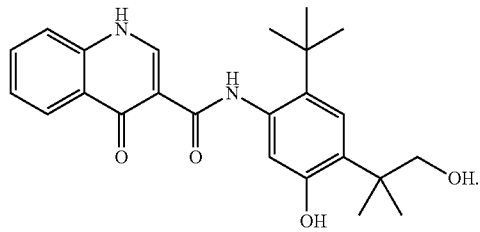 [SMILES: CC(C)(C)c1cc(C(C)(C)CO)c(O)cc1NC(=O)c1c[nH]c2ccccc2c1=O]

3. The method of claim 1, wherein the compound of Formula I has the structure:

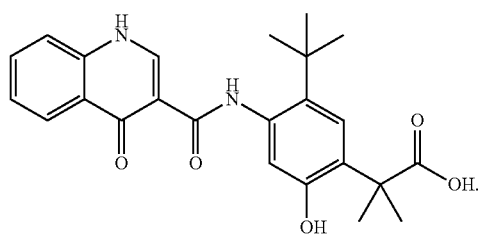 [SMILES: CC(C)(C)c1cc(C(C)(C)C(=O)O)c(O)cc1NC(=O)c1c[nH]c2ccccc2c1=O]

4. The method according to claim 1, wherein said disease is cystic fibrosis.

* * * * *